United States Patent
Shimer et al.

(10) Patent No.: US 10,773,054 B2
(45) Date of Patent: Sep. 15, 2020

(54) NEEDLE CANNULA-CATHETER BONDING METHOD AND APPARATUS

(71) Applicant: Medical Components, Inc., Harleysville, PA (US)

(72) Inventors: Kurt Shimer, East Norriton, PA (US); Matthew Gunn, Wayne, PA (US); Raymond Bizup, Feasterville, PA (US)

(73) Assignee: Medical Components, Inc., Harleysville, PA (US)

( * ) Notice: Subject to any disclaimer, the term of this patent is extended or adjusted under 35 U.S.C. 154(b) by 175 days.

(21) Appl. No.: 15/786,137

(22) Filed: Oct. 17, 2017

(65) Prior Publication Data
US 2018/0104442 A1 Apr. 19, 2018

Related U.S. Application Data

(60) Provisional application No. 62/408,919, filed on Oct. 17, 2016.

(51) Int. Cl.
*A61M 25/00* (2006.01)
*B29C 39/10* (2006.01)
(Continued)

(52) U.S. Cl.
CPC ........ *A61M 25/0014* (2013.01); *A61M 5/158* (2013.01); *A61M 25/0618* (2013.01);
(Continued)

(58) Field of Classification Search
CPC .............. A61M 5/158; A61M 25/0014; A61M 25/0606; A61M 5/3275; A61M 25/0631;
(Continued)

(56) References Cited

U.S. PATENT DOCUMENTS 4,106,506 A   8/1978 Koehn et al.
5,092,845 A   3/1992 Chang
(Continued)

OTHER PUBLICATIONS

International Search Report issued in co-pending International Patent Application No. PCT/US2017/056957, 7 pages (Apr. 5, 2018).

(Continued)

*Primary Examiner* — Tiffany Legette

(57) ABSTRACT

A cannula-catheter bonding method and apparatus can include a needle having a specifically configured connector end to reduce the risk of the connector end disengaging with an adapter (e.g., a catheter, a cannula, or a connector of a Huber needle assembly, etc.). The specifically configured needle connector end can be a formation, such as a barb, a bead, an annular structure, a rib, etc. The formation can be formed on the connector end, and may be elongated with a conical shaped nose leading to a base with a bottom. The formation can be used to prevent movement of the needle relative to the adapter. A method for producing the formation can include forming a mold for the formation in a plate, where the connector end can then be placed within the mold so that curable material can be disposed within the mold. Upon hardening of the curable material, the formation can take the shape of at least a portion of the mold.

13 Claims, 15 Drawing Sheets

(51) Int. Cl.
*B29C 65/48* (2006.01)
*A61M 5/158* (2006.01)
*A61M 25/06* (2006.01)
*B29C 35/08* (2006.01)
*A61M 5/32* (2006.01)

(52) U.S. Cl.
CPC .......... *A61M 25/0631* (2013.01); *B29C 39/10* (2013.01); *B29C 65/4845* (2013.01); *A61M 5/3275* (2013.01); *A61M 25/0606* (2013.01); *A61M 25/0625* (2013.01); *B29C 2035/0822* (2013.01); *B29C 2035/0827* (2013.01); *B29C 2035/0833* (2013.01)

(58) Field of Classification Search
CPC .......... A61M 25/0625; A61M 25/0009; A61M 39/12; A29C 39/10; A29C 39/4845; B29C 2035/0822; B29C 2035/0827; B29C 2035/0833

See application file for complete search history.

(56) References Cited

U.S. PATENT DOCUMENTS

2003/0204169 A1  10/2003  Howell et al.
2014/0316357 A1* 10/2014  Adams ............... A61M 1/0031
                                                            604/319

OTHER PUBLICATIONS

Written Opinion issued in co-pending International Patent Application No. PCT/US2017/056957, 10 pages (Apr. 5, 2018).

* cited by examiner

NEEDLE CANNULA-CATHETER BONDING METHOD AND APPARATUS

CROSS-REFERENCE TO RELATED APPLICATIONS

This application claims the benefit of U.S. provisional application 62/408,919 filed on Oct. 17, 2016, the entire contents of which is incorporated herein by reference.

FIELD OF THE INVENTION

Embodiments of the present invention relate to a method for bonding a needle connector end of a needle to a catheter or cannula, and in particular a method of generating needle having a specifically configured connector end to facilitate an improved bond between the needle and the catheter or cannula.

BACKGROUND OF THE INVENTION

Infusing fluid into a body of a patient is a common practice for a number of medical procedures and medical treatments. The fluid can be a drug use for treatment, a medication for therapy, a contrasting fluid used for imaging, etc. With such medical procedures and treatments, a catheter is generally inserted into the vascular system of the patient and the fluid is introduced through the catheter and into the patient. In some applications, an access port implanted into the body of the patient is used as a fluid reservoir from which fluid is dispensed. With such applications, fluid can be introduced into the access port via a catheter and then dispensed from the access port throughout a desired portion of the patient.

Typically, the access port includes a housing containing a reservoir that is capped with a needle-penetrable septum. With the access port implanted into the patient, a needle is inserted through the skin of a patient and through the septum so that the needle tip is positioned within the reservoir located below the septum. A connector end of the needle can still remain outside of the body of the patient so that a catheter or cannula can be connected to the connector end of the needle to facilitate flow of the fluid through the needle, into the access port reservoir, and then throughout the patient's body. Generally, a Huber needle or a Huber needle assembly is used when infusing fluid into the patient through an implanted access port. A Huber needle assembly can be a device that enables safe and effective insertion and retraction of a needle from the access port while also facilitating a fluid connection of the needle connector end to a fluid source via a catheter or cannula.

With some applications, it may be desired to infuse the fluid at a specific volume and/or rate to generate a desired flux of fluid passing into the access port and/or out-from the access port. To achieve this, a power injection technique can be used, whereby the fluid is introduced at high pressure, e.g., at least 400 pounds per square inch ("psi"). However, operating at such high pressure can cause the needle connector end to disengage with the catheter or cannula, or even cause the needle to dislodge from the Huber needle assembly, thereby creating a break in fluid communication between the catheter and/or cannula carrying the fluid and the reservoir of the access port.

The present invention is directed toward overcoming one or more of the above-identified problems.

SUMMARY OF THE INVENTION

The present invention can include a needle having a specifically configured needle connector end that can reduce the risk of the needle connector end disengaging with or dislodging from an adapter (e.g., a catheter, a cannula, or a connector of a Huber needle assembly, etc.). The specifically configured needle connector end can be a formation, such as a barb, a bead, an annular structure, a rib, etc. The formation can be formed on the needle connector end of the needle, and may be elongated with a conical shaped nose leading to a base with a bottom. The conical shape of the nose can facilitate easier engagement with the adapter because it is contemplated for the needle connector end, as well as the conical shaped nose, to spearhead the insertion of the needle into the lumen of the adapter. The adapter can be secured to the needle connector end with the application of a curable material (e.g., a material that is curable upon exposure of ultraviolet radiation). The formation can be used to prevent movement of the needle after the curable material has hardened. It should be noted that some exemplary embodiments refer to the formation as a barb, but the use of the term barb does not imply a particular shape. In fact the formation can be any type of arrangement or shape. The formation can include a bead of hardened polymer, for example.

A method for producing the formation (e.g., a barb or bead) can include forming a mold for the barb or bead in a plate. The needle connector end can then be placed within the mold so that curable material can be disposed within the mold. Upon hardening of the curable material, the barb or bead can take the shape of at least a portion of the mold. Hardening can be achieved by exposing the curable material to UV radiation. The needle connector end, along with the barb or bead, can then be inserted into a lumen of the adapter, which may include applying additional curable material to at least a portion of the needle connector end before inserting the needle connector end into the lumen of the adapter. The additional curable material can then be hardened with use of UV radiation.

In an exemplary embodiment, a method for creating a needle having at least one formation, the method comprises: inserting a needle connector end of a needle into a mold; introducing a curable material into the mold; and, causing the curable material to harden, forming at least one formation disposed around at least a portion of an outer surface of at least a portion of the needle connector end, wherein the at least one formation is capable of engaging with a catheter. Some embodiments include connecting the catheter to an adapter comprising at least one of a second catheter, a cannula, and a connector of a Huber needle assembly. Some embodiments include: the engagement of the at least one formation with the adapter facilitates fluid communication with a lumen of the adapter and a needle aperture of the needle; and, the engagement of the at least one formation with the adapter limits movement of the needle relative to the adapter while fluid exists within the lumen and the needle aperture. Some embodiments include the engagement of the at least one formation with the adapter limits movement of the needle relative to the adapter while the fluid is subjected to a differential pressure. Some embodiments include the causing the curable material to harden further comprises exposing the curable material to ultraviolet radiation. Some embodiments include the causing the curable material to harden generates a single formation of the curable material disposed around an entire circumference of the outer surface of a portion of the needle connector end. Some embodiments include the causing the curable material to harden forms the single formation exhibiting an elongated shape with a conical shaped nose portion leading to a base portion.

In another exemplary embodiment, a method for forming a bond between a needle and a catheter, the method comprises: providing a needle connector; depositing a first curable material onto at least a portion of an outer surface of at least a portion of the needle connector; causing the first curable material to harden, forming at least one formation disposed around the needle connector; introducing a second curable material on at least a portion of at least one of the needle connector end and the at least one formation; engaging the needle connector end with the catheter, wherein the catheter is slipped over at least a portion of the at least one formation; and causing the second curable material to harden forming a bond between the catheter and at least one of the needle connector and the at least one formation. Some embodiments include the bond between the catheter and at least one of the needle connector and the at least one formation limits movement of the needle relative to the catheter. Some embodiments include the bond between the catheter and at least one of the needle connector limits movement of the needle relative to the catheter while fluid existing within the needle and the catheter is subjected to a differential pressure. Some embodiments include the at least one formation is a bead of hardened polymer surrounding the needle connector.

In another exemplary embodiment, a method for forming a bond between a needle and an adapter, the method comprises: inserting a needle connector end of a needle into a mold; introducing a first curable material into the mold; causing the first curable material to harden, forming at least one formation disposed on at least a portion of an outer surface of at least a portion of the needle connector end; removing the needle connector end from the mold; introducing a second curable material on at least a portion of at least one of the needle connector end and the at least one formation; engaging the needle connector end with an adapter, the adapter comprising at least one of a catheter, a cannula, and a connector of a Huber needle assembly; and, causing the second curable material to harden forming a bond between the adapter and at least one of the needle connector end and the formation. Some embodiments include the at least one formation and the bond engage to reduce the risk of the needle disengaging with the adapter by limiting movement of the needle relative to the adapter. Some embodiments include: the adapter has an adapter first distal end and an adapter second distal end, the adapter first distal end configured to engage the at least one formation, the adapter second distal end configured to facilitate fluid communication with a fluid source; and, the engagement of the at least one formation with the bond prevents movement of the needle relative to the adapter in at least a forward longitudinal direction. Some embodiments include: the engagement of the needle connector end with the adapter facilitates fluid communication with a lumen of the adapter and a needle aperture of the needle; and, the engagement of the at least one formation with the bond limits movement of the needle relative to the adapter while fluid exists within the lumen and the needle aperture. Some embodiments include at least one of the causing the first curable material to harden and the causing the second curable material to harden further comprises exposing at least one of the first curable material and the second curable material to ultraviolet radiation. Some embodiments include the causing the first curable material to harden generated a single formation of the first curable material disposed around an entire circumference of the outer surface of a portion of the needle connector end. Some embodiments include the causing the first curable material to harden forms the at least one formation exhibiting an elongated shape with a conical shaped nose portion leading to a base portion. Some embodiments include connecting a catheter to the adapter. Some embodiments include the engagement of the at least one formation with the adapter limits movement of the needle relative to the adapter while the fluid existing within the needle and the adapter is subjected to a differential pressure. Some embodiments include the causing the first curable material to harden generates a single formation of the first curable material disposed around an entire circumference of the outer surface of a portion of the needle connector end.

In another exemplary embodiment, an assembly, comprises: a needle comprising a needle connector end, a needle tip, and a needle shaft extending between the needle connector end and the needle tip; at least one formation formed on at least a portion of the needle connector end; and, a catheter having a lumen, wherein the catheter covers the needle connector end and the formation. Some embodiments include a curable material disposed on at least a portion of at least one of the needle connector end and the at least one formation before the lumen engages the needle connector end and the formation, the curable material having cured thereafter. Some embodiments include the at least one formation is curable material that had been caused to cure. Some embodiments include the at least one formation has an elongated shape with a conical shaped nose portion leading to a base portion. Some embodiments include the at least one formation is a single formation disposed around an entire circumference of an outer surface of a portion of the needle connector end.

In another exemplary embodiment, a method for creating a needle having at least one formation, the method comprises: securing a needle connector end of a needle to a support, wherein the needle comprises a needle shaft, a needle tip at a first distal end of the needle, the needle connector end at a second distal end of the needle, and a needle aperture extending through the needle; introducing a first curable material into a portion of the support where the needle connector end is secured via a gun applicator; causing the first curable material to harden; securing the needle having the at least one formation formed thereon into a rotatable spring-clamp assembly; applying a second curable material to at least a portion of the needle connector end via the gun applicator; securing an adapter to an adapter guide, aligning a lumen of the adapter with the needle connector end; translating the adapter guide towards the rotatable spring-clamp assembly until at least a portion of the at least one formation is within the lumen; and, causing the second curable material to at least one of harden and adhere to at least one of a portion of the needle, a portion of the at least one formation, and a portion of the adapter. Some embodiments include the support further comprising a mold into which the needle connector end is inserted. Some embodiments include: the mold is formed into a plate; the plate is positioned over a septum/pin mount, the septum/pin mount located within a septum/pin mount pocket of the support; and, the septum/pin mount comprises a pin that protrudes through the mold. Some embodiments include securing the needle to the support further comprises allowing the pin to insert into the needle aperture. Some embodiments include securing the needle to the support further comprises immobilizing the needle with a swivel arm of the support. Some embodiments include securing the needle to the support further comprises ensuring proper placement and alignment of the needle connector end within the mold by at least one of: inserting the pin into the needle aperture of the needle connector end with a longitudinal axis of the needle connector end being coaxial with the pin; causing a distal end of the needle connector end to be adjacent a septum of the septum/pin mount; and, causing the distal end of the needle connector end to be flush with an upper surface of the septum. Some embodiments include applying the second curable material further comprises rotating the rotatable spring-clamp assembly to cause the needle to rotate. Some embodiments include translating the adapter guide towards the rotatable spring-clamp assembly further comprises rotating the rotatable spring-clamp assembly to cause the needle to rotate. Some embodiments include applying additional second curable material where the adapter and needle connector interface before causing the second curable material to at least one of harden and adhere. Some embodiments include rotating the rotatable spring-clamp assembly to cause the needle to rotate while applying additional second curable material. Some embodiments include sliding the support via a slide track into an electromagnetic radiation emitter assembly. Some embodiments include activating an electromagnetic radiation emitter of the electromagnetic radiation emitter assembly, causing the first curable material to harden and form at least one formation disposed on at least a portion of the needle connector end. Some embodiments include comprising sliding the support via a slide track out from the electromagnetic radiation emitter assembly. Some embodiments include emitting electromagnetic radiation from an electromagnetic radiation emitter of the rotatable spring-clamp assembly to cause the second curable material to at least one of harden and adhere. Some embodiments include the at least one formation exhibits a tapered shape. Some embodiments include the at least one formation is a bead of hardened polymer surrounding the needle connector.

In another exemplary embodiment, a mold for generating at least one formation on a needle connector end of a needle, comprises: a plate with at least one cavity having an open top and sidewalls conjoined with a bottom, the bottom formed into a portion of the plate, the at least one cavity configured for receiving the needle connector end of the needle therein, the needle comprising an outer surface and a lumen formed within the needle, the mold further configured for receiving a material introduced within the at least one cavity adjacent the needle connector end outer surface, the material comprising a substance that transitions from a liquid form to a solid form upon exposure to a condition to generate the at least one formation; wherein at least one of the a portion of the sidewalls and the bottom substantially conforms to a portion of the needle connector end so that a contact between the needle connector end and the sidewalls and/or bottom forms a fluid seal to prevent the material in its liquid form from traveling into the lumen; wherein upon the material transitioning to the solid form, the at least one formation takes a shape that substantially matches a profile of the at least one cavity. Some embodiments include the profile of the at least one cavity generates a fill space to receive the material, the fill space being adjacent the needle connector end outer surface. Some embodiments include the fill space surrounds an entire circumference of at least a portion of the needle connector end outer surface. Some embodiments include the portion of the sidewalls that substantially conforms to a portion of the needle connector end prevents the material, in its liquid form, from traveling to a distal end of the needle connector end, wherein the distal end of the needle connector end rests upon the bottom. Some embodiments include the profile of the at least one cavity exhibits a tapered shape. Some embodiments include the profile of the at least one cavity exhibits an elongated shape with a conical shaped nose portion leading to a base portion. Some embodiments include the at least one cavity is a single cavity and the profile of the single cavity is configured to generate a single formation. Some embodiments include the plate is disc shaped and the mold is located in a center portion of the plate. Some embodiments include at least a portion of the plate comprises polytetrafluoroethylen. Some embodiments include a septum/pin mount having a pin configured to protrude through the bottom of the plate and into the mold. Some embodiments include the material transitions from the liquid to the solid upon exposure to at least one of ultra-violet radiation, air, a certain temperature, and an ultrasonic wave.

While these potential advantages are made possible by technical solutions offered herein, they are not required to be achieved. The presently disclosed method and apparatus can be implemented to achieve technical advantages, whether or not these potential advantages, individually or in combination, are sought or achieved.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present invention will be more apparent from the following more particular description thereof, presented in conjunction with the following Figures, in which:

FIG. 5A shows a needle being inserted into a mold, FIG. 5B shows a first curable material being inserted into the mold, FIG. 5C shows the needle removed from the mold after the first curable material has been cured, FIG. 5D shows second curable material being applied to the needle connector end, FIG. 5E shows the needle connector end being inserted into the adapter, and FIG. 5F shows the needle with specifically configured connector end bonded to the adapter after the second curable material has been cured.

DETAILED DESCRIPTION OF THE INVENTION

The following description is of an embodiment presently contemplated for carrying out the present invention. This description is not to be taken in a limiting sense, but is made merely for the purpose of describing the general principles and features of the present invention. The scope of the present invention should be determined with reference to the claims.

Figure 1:
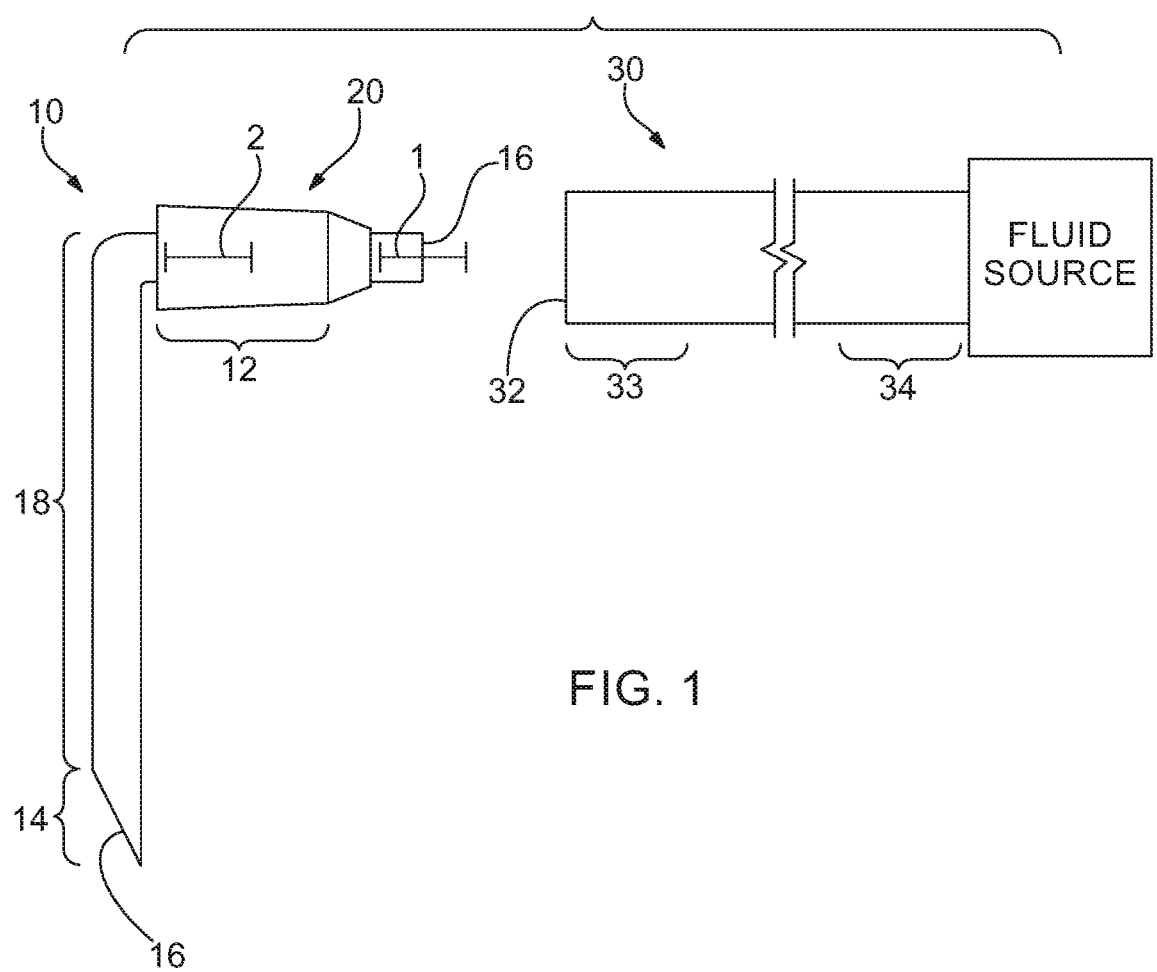
FIG. 1 shows an exemplary needle having a specifically configured formation on the needle connector end in juxtaposition with an adapter.

Referring to FIG. 1, embodiments of the present invention relate to a needle 10 having a needle connector end 12 with a formation 20, and a method of producing the formation 20 and further generating a bond between the formation 20 and an adapter (e.g., a catheter, a cannula, or a connector of a Huber needle assembly, etc.) 30. In some embodiments, the connector end 12 with the formation 20 can prevent, or at least reduce the risk of, the needle connector end 12 disengaging with or dislodging from the adapter 30. This can include reducing the risk of disengagement of the needle connector end 12 with the adapter 30 while fluids are being infused through the needle 10 via the adapter 30. This can further include reducing the risk of disengagement of the needle connector end 12 with the adapter 30 while fluids are infused through the needle 10 via the adapter 30 while the fluid is under a differential pressure.

The needle 10 can include an elongated, tubular structure having a cylindrical shape with a needle tip end 14, a needle connector end 12, and an aperture 16 extending through the needle 10 from the needle tip end 14 to the needle connector end 12. The needle tip end 14 may be beveled to facilitate insertion into an object via puncturing. The needle 10 may be fabricated from metal, ceramic, polymer, etc. In at least one embodiment, the needle 10 is fabricated from stainless steel. The needle connector end 12 can be structured to be slidably engaged with an adapter 30, which can include the needle connector end 12 sliding within the adapter 30. (See FIG. 3) It is contemplated for the adapter 30 to include a lumen 32 into which the needle connector end 12 slidingly engages. For example, the needle connector end 12 can be slid within a first distal end 33 of an adapter 30 so as to insert within the lumen 32 of the adapter, wherein a second distal end 34 of the adapter 30 can be connected to a fluid source. The needle 10 can include a shaft 18 portion existing between the needle tip end 14 and the needle connector end 12. The needle 10 can be structured to extend linearly from the needle tip end 14 to the needle connector end 12. Alternatively, any portion of the needle shaft 18 can include an angle. For example, a portion of the needle shaft 18 can exhibit a ninety-degree angle such that the needle 10 forms an "L" shape. Other shapes and angles can be used, such as but not limited to, curvelinear shapes, arch shapes, forty-five degree angles, sixty-degree angles, etc. Furthermore, the needle 10 can be structured to be part of a Huber needle assembly or be temporarily retained within the Huber needle assembly.

The needle connector end 12 can include at least one formation 20. The formation 20 can be structured to be slidingly engaged by the adapter 30 along with the needle connector end 12. The presence of the formation 20 at the needle connector end 12 can be used to prevent, or at least reduce the tendency of, the needle connector end 12 becoming disengaged with the adapter 30. This can include reducing the tendency of the needle connector end 12 becoming disengaged with the adapter 30 when fluid is introduced through the adapter 30 and into the needle aperture 16 at a high pressure (e.g., 400 psi to 600 psi).

Figure 2A:
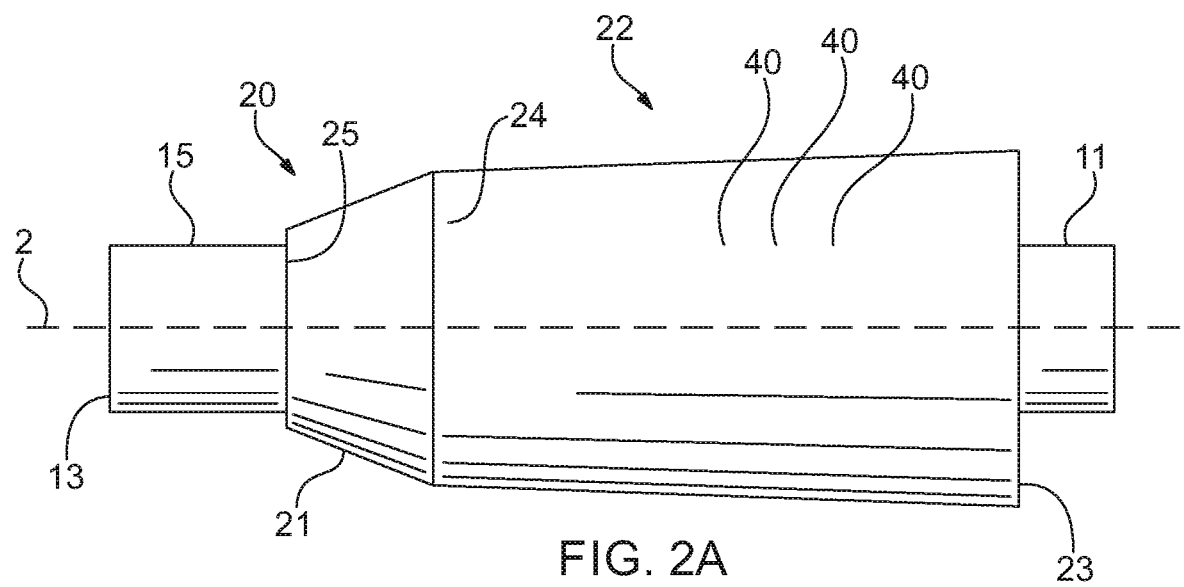
FIG. 2A shows an exemplary needle connector end with a formation on a portion thereof.
Figure 2B:
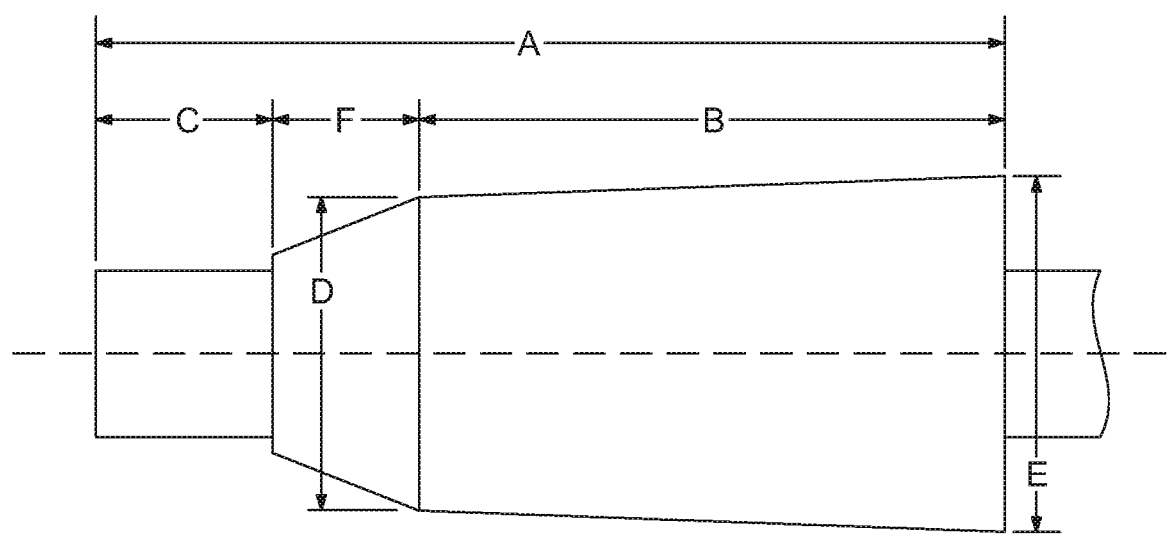
FIG. 2B shows the needle connector with the formation exhibiting exemplary dimensions.

Referring to FIGS. 2A-2B, the formation 20 can be a formation disposed on an outer surface 11 of the needle 10. The formation can be any shape. For example, the formation can be a bead of hardened polymer surrounding the needle connector end 12. As will be explained later, the formation 20 can be formed from a first curable material 40. The formation 20 can be disposed on any portion of the outer surface 11, which may include at least one sectant of the outer surface 11. Alternatively, the formation 20 can be disposed around the entire circumference of at least a portion of the outer surface 11. For example, the formation 20 may be disposed around an entire circumference of a portion of the outer surface 11 of the needle 10 at the needle connector end 12. In some embodiments, the formation 20 can be a formation exhibiting a conical shaped nose 21 portion leading to a base portion 22. Further, the formation 20 can be elongated, with both the base 22 and the conical shaped nose 21 extending along a longitudinal axis 2. In further embodiments, the formation 20 is elongated along its longitudinal axis 2, wherein the formation's longitudinal axis 2 is coaxial, or at least parallel, with the longitudinal axis 1 of the needle connector end 12. The longitudinal axis 1 of the needle connector end 12 can be coaxial with the needle aperture 16 at the needle connector end 12, and may run along a central line of the needle aperture 16 of the needle connector end 12. (See FIG. 1). In some embodiments, the conical shaped nose 21 forms a bevel with the needle outer surface 11. Alternatively, the conical shaped nose 21 can form a chamfer with the needle outer surface 11. The base 22 can exhibit a straight shape, curvilinear shape, sinsusoidal shape, a taper, etc. For example, the base 22 can be tapered so as to flare out as it runs towards a base bottom 23. This can include flaring out from the nose-base interface 24 to the base bottom 23. In other words, the width (e.g., an outer diameter) of the formation 20 at the nose-base interface 24 can be less than the width of the formation 20 at the base bottom 23. The taper can be continuous or stepped. The base bottom 23 can be flat (e.g., shaped to be perpendicular with the longitudinal axis 2), convex, concave, etc. The nose 21 can include a nose tip 25 that may extend to the distal end 13 of the needle connector end 12 so as to cover the distal end 13 of the needle connector end 12. In other embodiments, the nose tip 25 can interface with the needle outer surface 11 at a distance away from the distal end 13 of the needle connector end 12 so as to form an exposed connector end 15.

In an exemplary embodiment, the formation 20 is disposed around an entire circumference of a portion of the needle outer surface 11 at the needle connector end 12. The formation 20 is elongated with the conical shaped nose 21 leading to the base 22, both of which extend along the longitudinal axis 2. Further, the formation 20 is elongated along the longitudinal axis 1 of the needle connector end 12. The base 22 has a length B, as measured along the longitudinal axis 2 and from the base bottom 23 to the nose-base interface 24. The conical shaped nose 21 has a length F, as measured along the longitudinal axis 2 and from the nose-base interface 24 to the nose tip 25. B is greater than F. The conical shaped nose 21 forms a bevel with the needle outer surface 11. The base 22 exhibits a taper so that the width at the nose-base interface 24 is D, the width at the base bottom 23 is E, and D is less than E. The taper is continuous from the nose-base interface 24 to the base bottom 23. The base bottom 23 has a flat shape. The nose tip 25 interfaces with the needle outer surface 11 at a distance C from the distal end 13 of the needle connector end 12, forming the exposed connector end 15 having a length C. The length from the base bottom 23 to the distal end 13 of the connector end 12 is A.

Some exemplary dimensions that may be used are displayed in Table 1.

TABLE 1

Exemplary dimensions in inches.

| Dimension (REF) | 22Ga | 20Ga | 19Ga |
|---|---|---|---|
| A | .135"-.185" | .135"-.185" | .135"-.185" |
| B | .080"-.100" | .080"-.100" | .080"-.100" |
| C | .030"-.060" | .030"-.060" | .030"-.060" |
| D | .042" | .054" | .065" |
| E | .049"-.059" | .060"-.070" | .070"-.080" |
| F | .020"-.025" | .020"-.025" | .020"-.025" |

Dimension Analysis

Dimension A—Dimension A can be important to the manufacturing process. Having the formation 20 (e.g., glue bead) to close to the needle edge 13 may results in occlusions/flash at the needle opening. It also may make it difficult for an operator to guide the adapter 30 (e.g., tubing) over the glue bead 20 during manufacturing. Having the glue bead 20 too far away from the needle's edge 13 may require the tubing 30 to be positioned over the glue bead 20 further up the needle 10. This potentially allows the front, uncured glue bead 20 (during the bonding operation) to contact the needle-tubing bonding fixture, which may lead to the needle 10 becoming adhered to the fixture's metal surfaces.

Dimensions B, D, & E—The length/height of the glue bead 20 can aid in bonding/sealing strength of the needle/extension joint. The length/height may be important in preventing leakage as the tubing 30 expands over the glue bead 20. The compressive strength of the stretched tubing 30 can aid in the joint's seal. There may be a slight draft on the glue bead 20 that can allow the bead 20 to slide out from the curing fixture easily. The draft may also help the operator advance the tubing 30 over the glue bead 20 more easily, hence dimension D can be smaller than dimension E. If any of these dimensions are out of specification, it may lead to leakage (i.e., the formation 20 is too small), or may cause issues during manufacturing as the tubing 30 cannot be advanced (i.e., the formation 20 is too large).

Dimension C—If this dimension is too short, occlusions/flash at the needle opening may occur. If this dimension is too long, it may result in a longer bond length, potentially causing issues during the bonding operation (see Dimension A's explanation).

Dimension F—The back taper can be used to guide/expand the tubing 30 over the glue bead 20. Without this feature, it may be difficult for an operator to consistently expand the tubing 30 inner diameter over the glue bead 20 during manufacturing.

Figure 3:
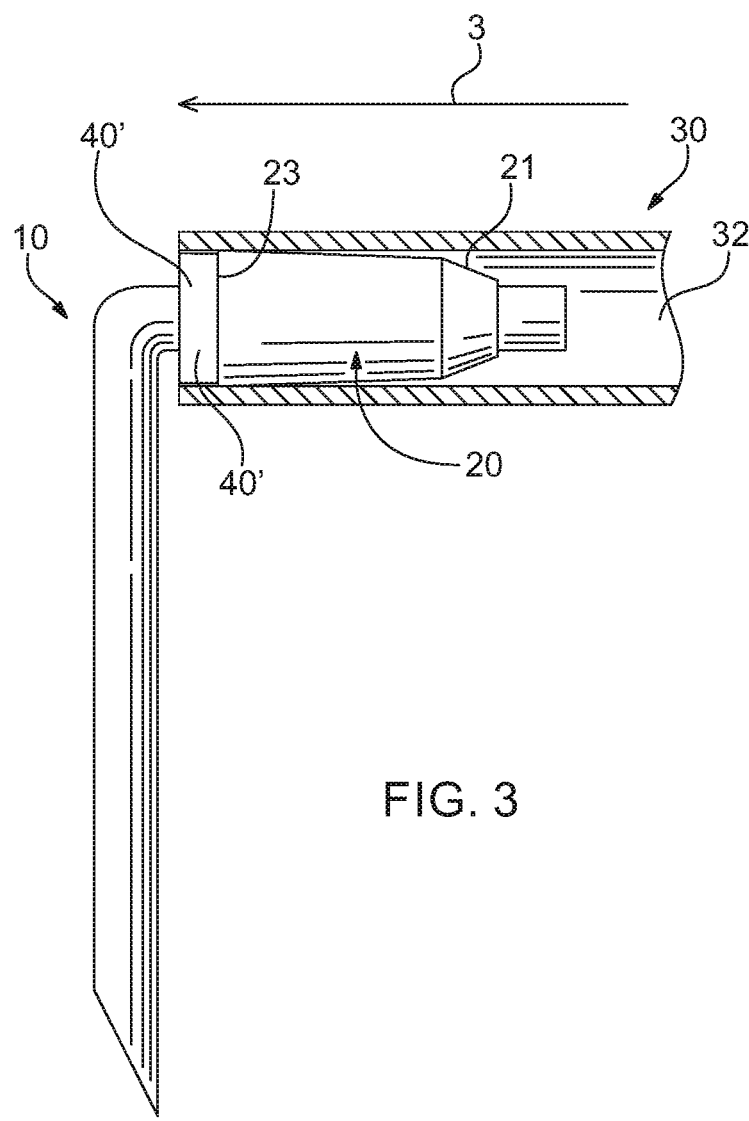
FIG. 3 shows an exemplary needle with a specifically configured needle connector end inserted into a portion of the adapter.

Referring to FIG. 3, the conical shape of the nose 21 can facilitate easier engagement with the adapter 30. For example, it is contemplated for the needle connector end 12, as well as the conical shaped nose 21, to spearhead the insertion of the needle 10 into the lumen 32 of the adapter 30. While the adapter 30 may be flexible and resilient, the inner diameter (i.e., the lumen 32) of the adapter 30 may be equal to or lesser than width D, and thus the beveled sides of the nose 21 can allow easier introduction of the formation 20 portion of the needle connector end 12 into the adapter's lumen 32. As will be explained later, the adapter 30 can be secured to the needle connector end 12 with the application of a second curable material 40'. The second curable material 40' can be placed at the base bottom 23 before the adapter 30 is slid over the needle connector end 12, wherein the second curable material 40' can be allowed to harden afterwards. Upon hardening, the second curable material 40' can adhere to the adapter 30, which may also include adhering to the formation 20 and/or needle outer surface 11. The shape of the base bottom 23 can facilitate the base bottom 23 to act as a backstop and abut against the hardened second curable material 40' and prevent movement of the needle 10 in the longitudinal forward direction 3. For example, a flat base bottom 23 can be used to ensure that a desired surface area of the base bottom 23 abuts against the hardened second curable material 40' to prevent movement of the needle 10 in the longitudinal forward direction 3. As another example, the second curable material 40' can be made to adhere to the formation 20 as well as the adapter 30, and thus a convex shaped base bottom 23 or even a conical shaped base bottom 23 can be used to increase the surface area by which the second curable material 40' makes contact with the formation 20. Increasing the surface area may generate a stronger bond. Other ways to increase the surface area can be to spline, rib, or tooth the formation 20 or base bottom 23.

Any curable material 40, 40' used in this disclosure can be a thermosetting polymer or resin for example, that hardens and/or adheres upon exposure to electromagnetic radiation (i.e., curing the material). This can be infrared ("IR") radiation, ultraviolet ("UV") radiation, etc. Further, the first curable material 40 can be the same or different from the second curable material 40'. It is contemplated to use UV curable materials, such as monomers and/or oligomers with photoinhibitors to transform the monomer and/or oligomer from a liquid to a solid upon exposure to a particular frequency (e.g., UV radiation) of electromagnetic radiation. These can include, but are not limited to, polyester, polyurethane, epoxy resin, polymides, acrylic adhesives, etc. An example curable material may be 3921 Locktite® Light Cure Acrylic Adhesive, which is a preferred material because it is a medically safe UV curable acrylic adhesive with viscosity properties that work well with the inventive process.

Figure 4A:
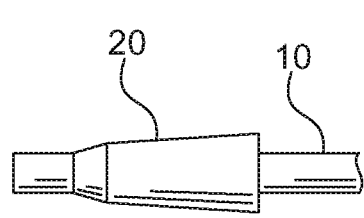
FIG. 4A shows an exemplary formation on a twenty-two gauge ("GA") needle.
Figure 4B:
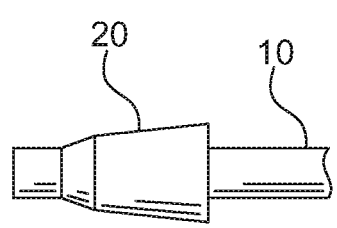
FIG. 4B shows a formation on a twenty GA needle.
Figure 4C:
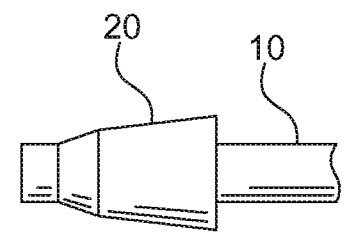
FIG. 4C shows a formation on a nineteen GA needle.

It is understood that different size needles 10 (e.g. different gauge, inner diameter, wall thickness, etc.) may require different size formations 20. This is shown with FIGS. 4A-C, where FIG. 4A is a formation 20 formed on a twenty-two gauge ("GA") needle 10, FIG. 4B is a formation 20 formed on a twenty GA needle 10, and FIG. 4C is a formation 20 formed on a nineteen GA needle 10. For example, referring to FIGS. 4A-4C, a formation 20 for a twenty-two GA needle 10, which is typically a measure of the outer diameter of the needle 10, may be smaller, or at least have widths D and E that are smaller than widths D and E of a formation 20 for a nineteen GA needle 10. It is further contemplated that the size of the formation 20, including the lengths A, B, and F and widths D and E, may depend more on the sizes of the adapter 30 and the lumen 32 of the adapter 30 rather than the size of the needle 10. Thus, the size of the formation 20 can be made to engage the adapter 30, fit into the lumen 32, generate a desired surface area of the formation 20, etc., regardless of the gauge of the needle 210.

Figure 5A:
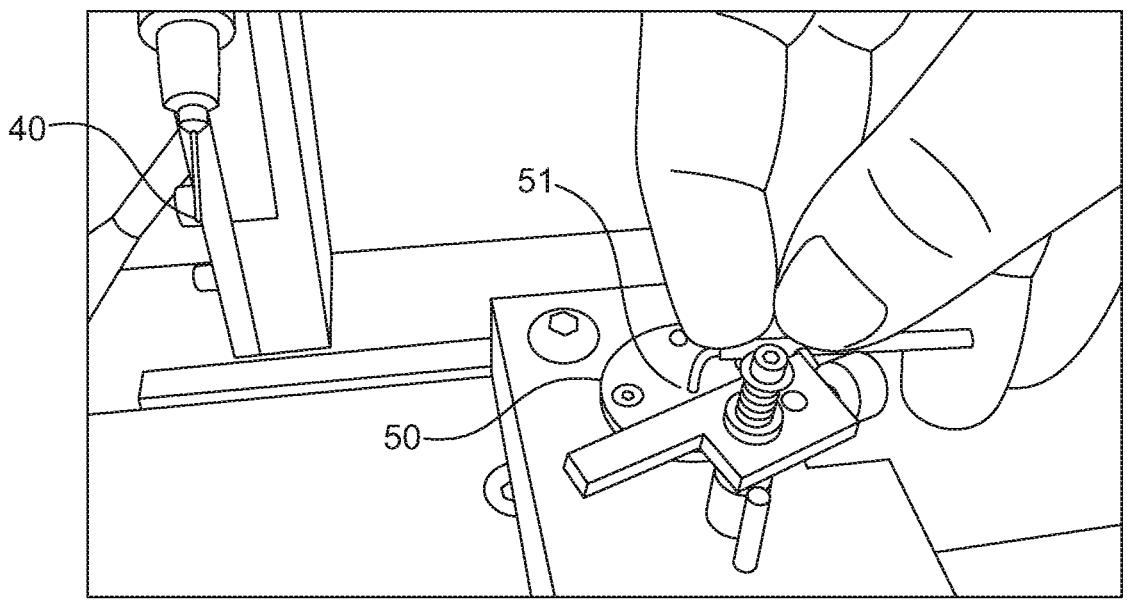
FIGS. 5A-5F show an exemplary method of forming a bond between a needle connector end and an adapter, where
Figure 5B:
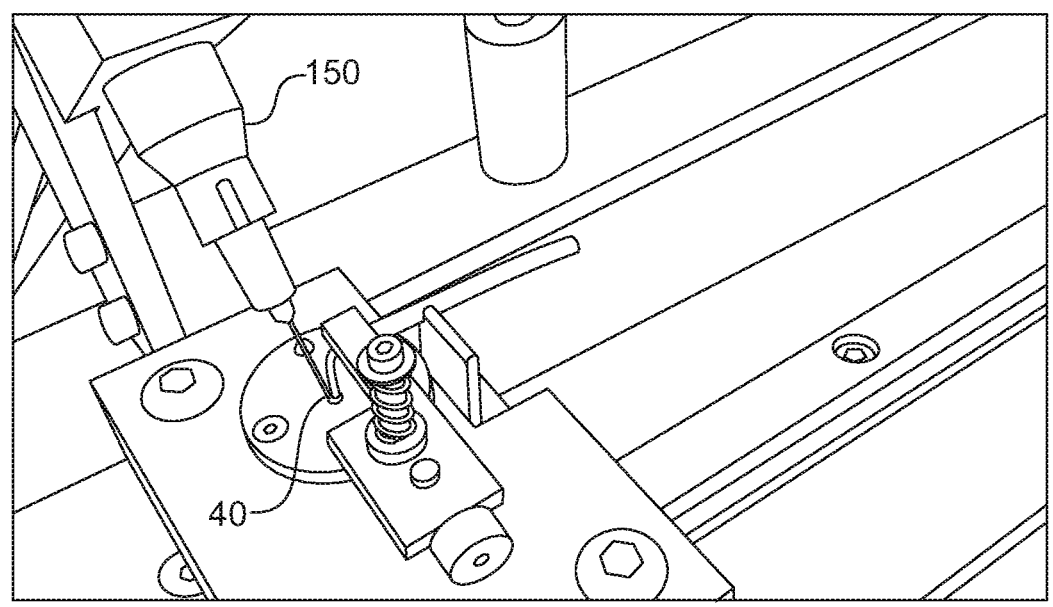
Figure 5C:
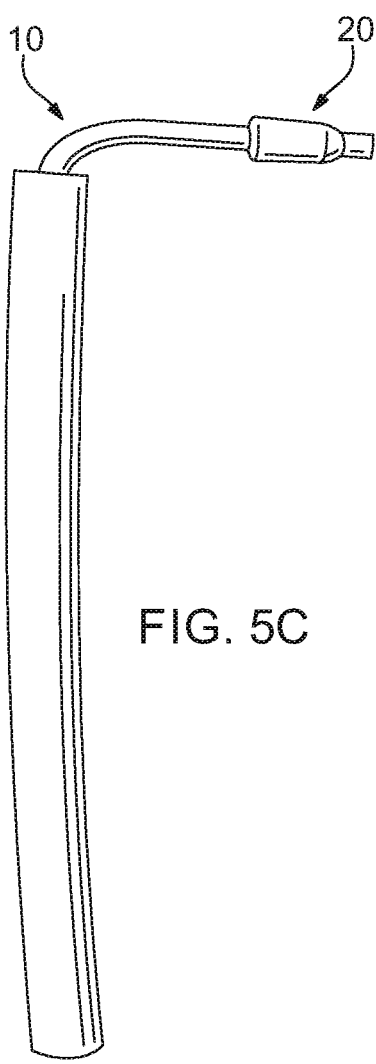
Figure 5D:
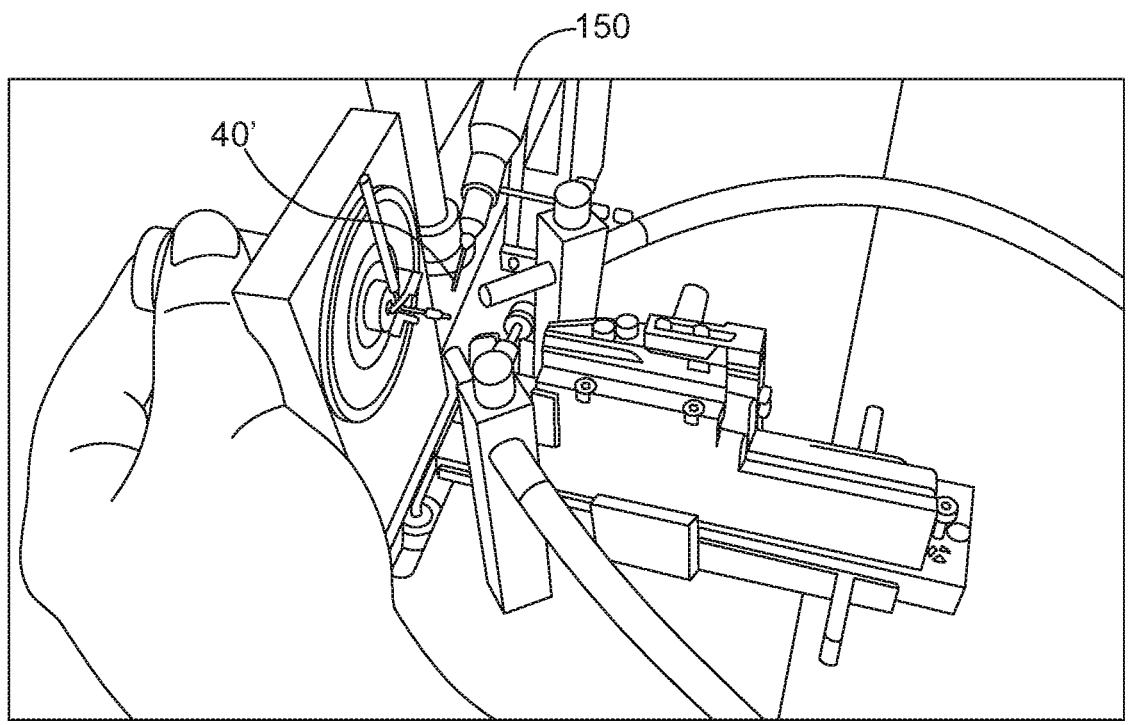
Figure 5E:
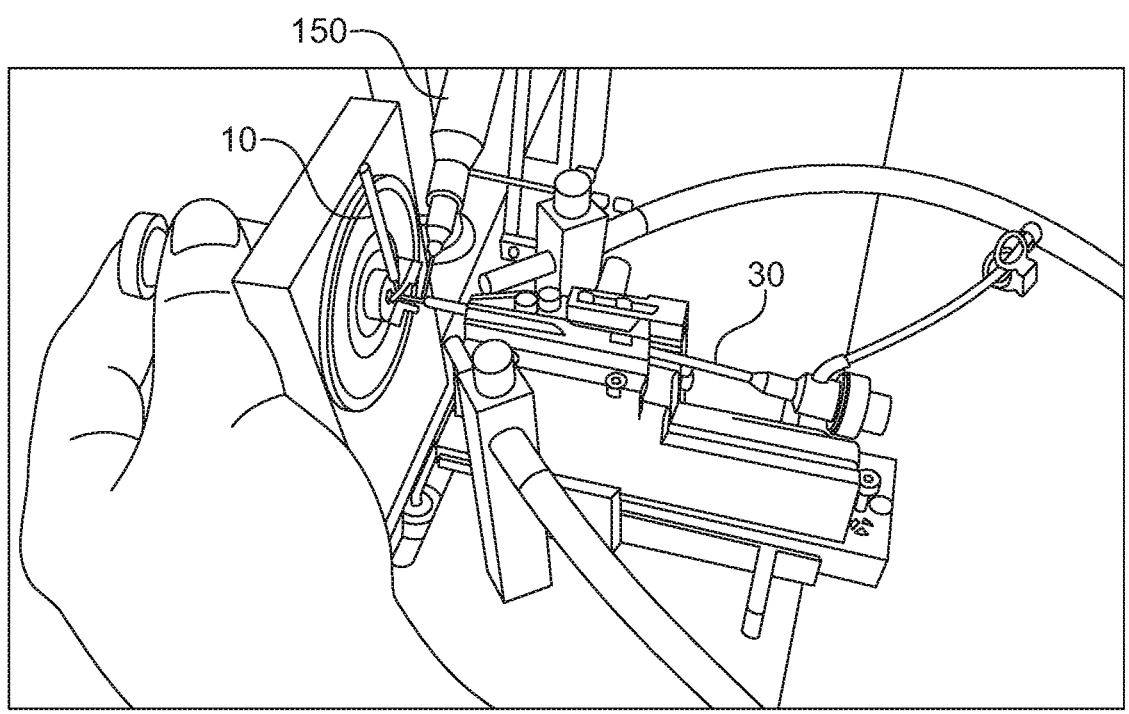
Figure 5F:
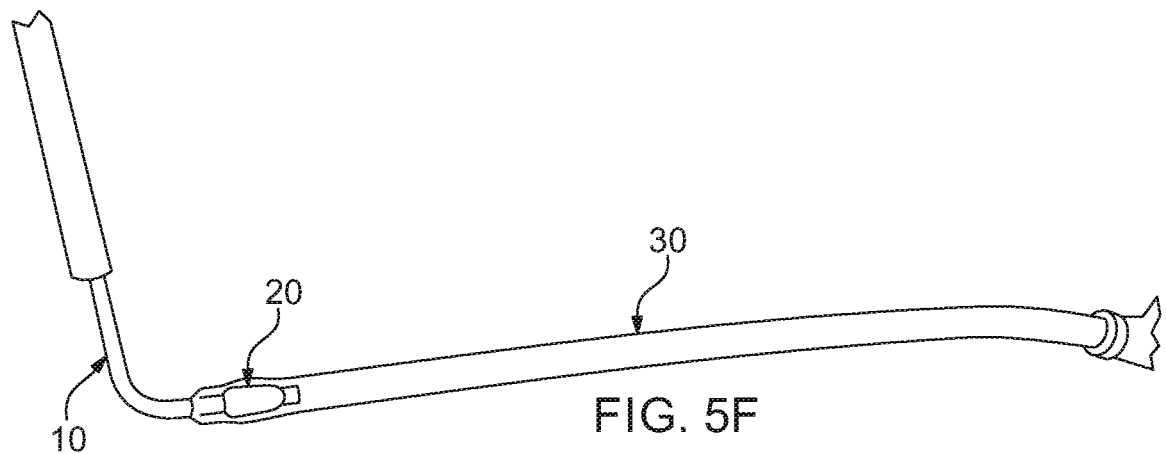

Referring to FIGS. 5A-5F, a method of forming a bond between the needle connector end 12 and the adapter 30 can be achieved by following the basic steps outlined below. A mold 51 can be formed into a plate 50, the mold 51 including a cavity in the plate 50. The needle connector end 12 can then be inserted into the mold 51 and held in place, as shown in FIG. 5A. The first curable material 40 can then be introduced into the mold 51, as shown in FIG. 5B. This can be achieved by introducing the first curable material 40 via a gun applicator 150. Afterwards, the first curable material 40 can be hardened to form the formation 20 around the needle outer surface 11 at the needle connector end 12. The mold 51 can act as a means for casting for the formation 20; therefore, the mold 51 can exhibit a shape matching that of the formation 20 to be produced. To form the formation 20, the first curable material 40 can be exposed to UV radiation until the first curable material 40 hardens and adheres to the needle connector end 12. The needle 10 can then be removed from the mold 51, as shown in FIG. 5C. The second curable material 40' can be applied to at least a portion of the needle connector end 12, as shown in FIG. 5D. This can include applying the second curable material 40' to at least one of a portion of the exposed connector end 15, a portion of the formation 20, and a portion of the needle shaft 18. A portion of the needle 10 can then be slidably inserted into the adapter 30, which may include inserting the needle connector end 12 into the lumen 32 of the adapter 30, as shown in FIG. 5E. This may include causing the needle connector end 12 to spearhead the insertion. Afterwards, the second curable material 40' can be exposed to UV radiation until the second curable material 40' hardens and/or adheres to at least one of the needle connector end 12, the needle shaft 18, the formation 20, and the lumen 32. The resultant structure is a needle 10 with a needle connector end 12 having a formation 20, where the needle connector end 12 is bonded to an adapter 30, as shown in FIG. 5F.

With referenced to FIGS. 6-15, a more detailed explanation of each method step for forming a bond between the needle connector end 12 and the adapter 30 is disclosed.

Figure 6A:
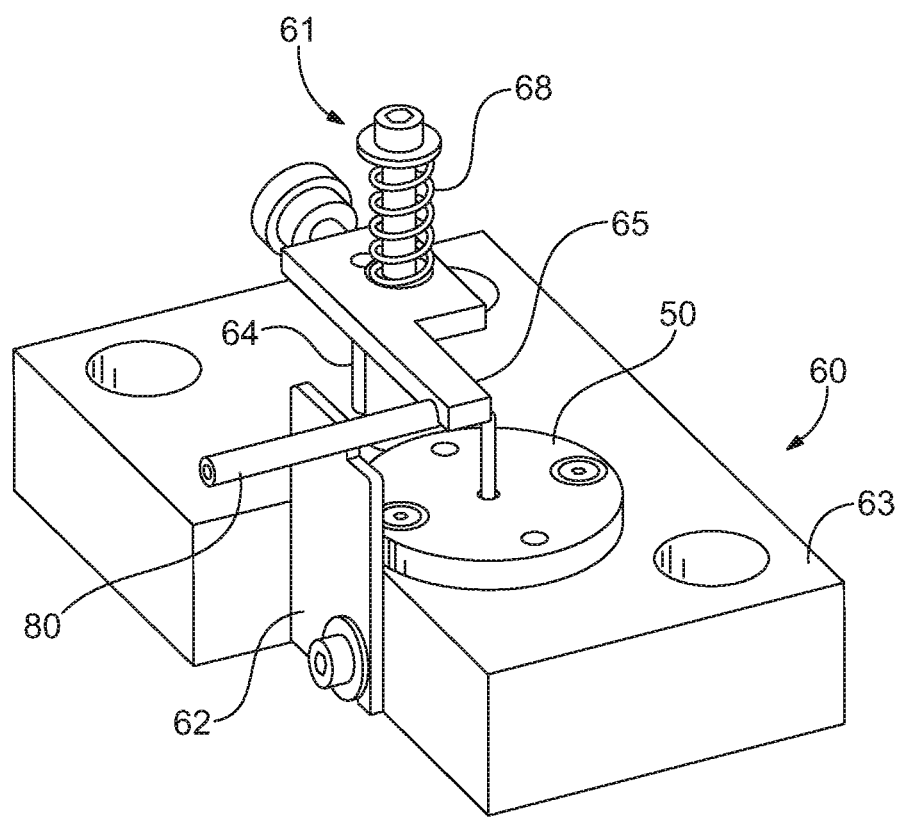
FIGS. 6A-6B show a support in an assembled state and the support in a disassembled state, respectively, that may be used with the method.
Figure 6B:
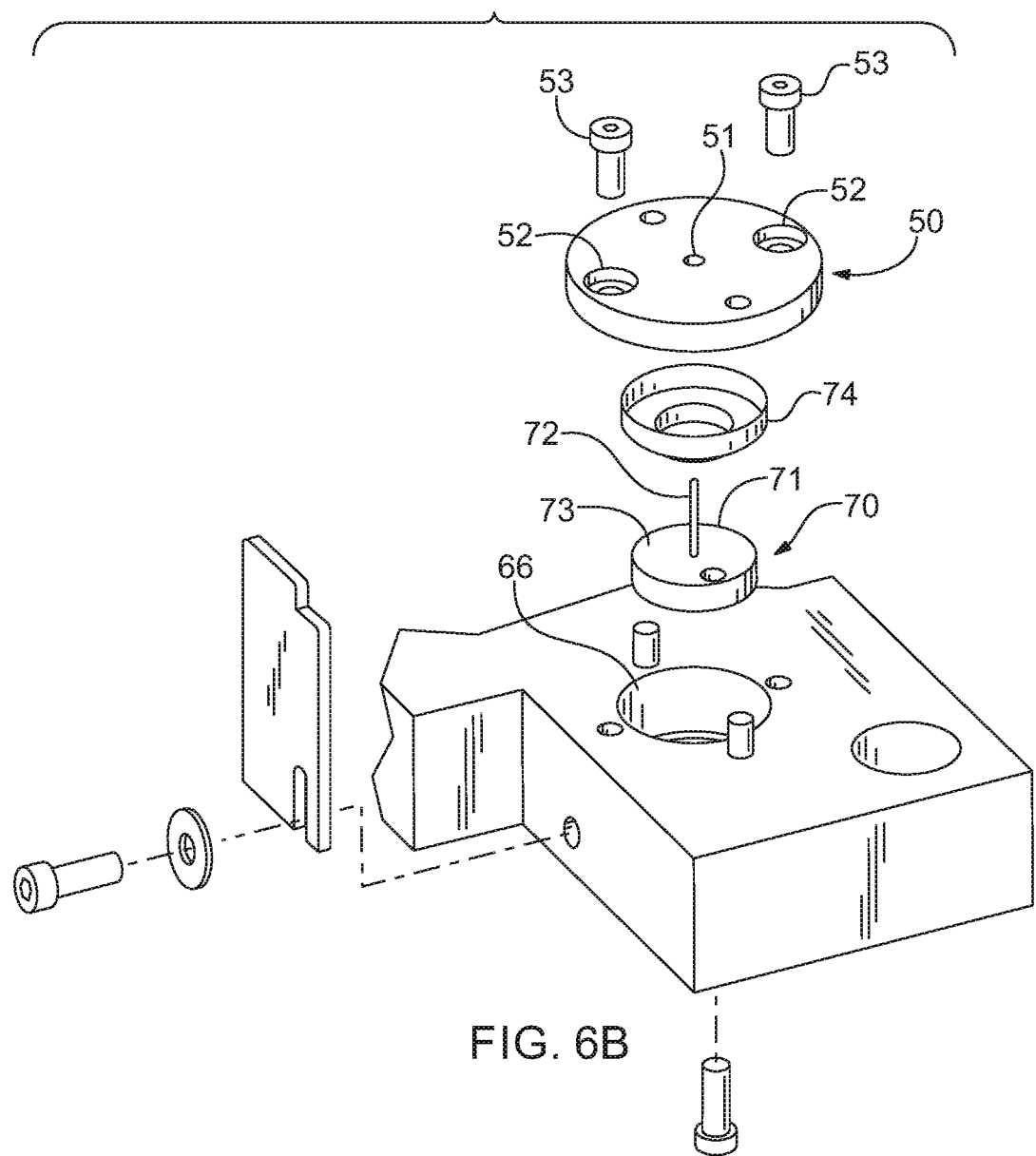

FIGS. 6A-6B show a support 60 in an assembled state and the support 60 in a disassembled state, respectively. A support 60 with a first needle clamp 61 and a needle bracket 62 can be used to secure the needle 10 in place. The support 60 can be a polyoxymethylene (e.g, Derlin®) block structure with the first needle clamp 61 extending perpendicularly from a flat support upper surface 63 and the needle bracket 62 extending from a side surface 64 of the support 60, wherein the needle bracket 62 can also extend perpendicularly with respect to the support upper surface 63. The first needle clamp 61 can include a stationary post 64 with a swivel arm 65 attached thereto. The swivel arm 65 can further include a spring-loaded elevation adjustment mechanism. The spring-loaded swivel arm 65 arm can rotate about the post 64, and the elevation of the spring-loaded swivel arm 65 can be changed relative to the post 64 by compression and expansion of a spring 68 of the spring-loaded elevation adjustment mechanism. The support 60 can further include a septum/pin mount pocket 66 configured to receive a septum/pin mount 70. The septum/pin mount 70 can be a disc-shaped member 71 with a pin 72 extending perpendicularly from a disc top 73. Further, the pin 72 can be inserted through a septum 74 (e.g., a silicon member) so as to secure the septum 74 onto the disc-shaped member 71. The septum/pin mount pocket 66 can slidably receive the septum/pin mount 70 so that the pin 72 extends perpendicularly from a geometric plane of the support upper surface 63.

Figure 7A:
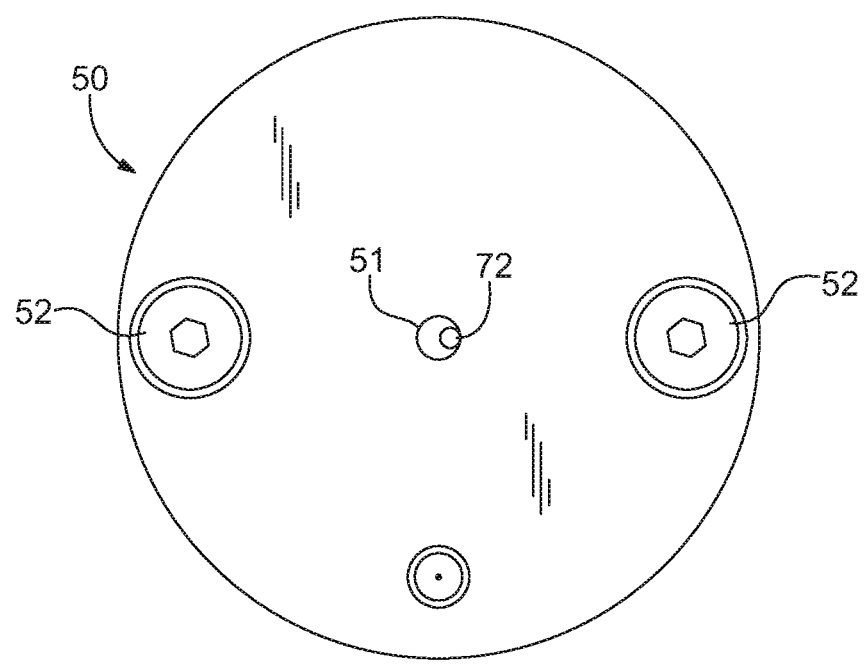
FIG. 7A shows a plate positioned on a septum/pin mount with a pin off-centered within a mold.
Figure 7B:
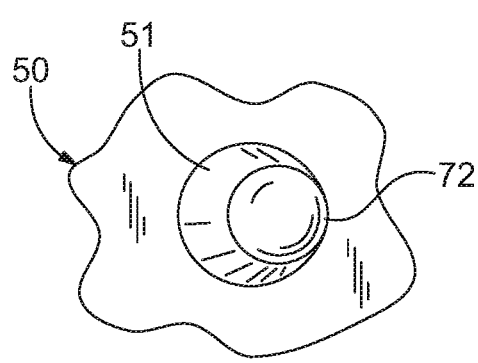
FIG. 7B shows a close up view of FIG. 7A.
Figure 7C:
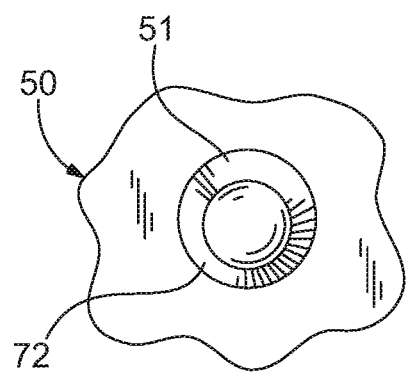
FIG. 7C shows a close up view with the pin centered within the mold.

Referring to FIGS. 7A-7C, after placement of the septum/pin mount 70 within the septum/pin mount pocket 66, the plate 50 can be placed on top of the septum/pin mount 70 such that the pin 72 protrudes through the mold 51 within the plate 50. The plate 50 can be adjusted to ensure that the pin 72 is centered within the mold 51. For example, FIG. 7A shows the plate 50 positioned on the septum/pin mount 70 with the pin 72 off-centered. FIG. 7B is a close up view of FIG. 7A. FIG. 7C is a close up view showing the pin 72 centered within the mold 51. The plate 50 can be a polytetrafluoroethylen (e.g, Teflon®) disc-shaped object with the mold 51 formed into a central portion of the plate 50. The plate 50 can further include at least one pin-mount fastener aperture 52 and at least one pin-mount fastener 53 to facilitate securing the plate 50 to the support 60 and holding the septum/pin mount 70 in place. Once properly centered, the plate 50 can be secured in place with the use of the pin-mount fasteners 53.

As noted above, different needles 10 (e.g. different gauge, inner diameter, wall thickness, etc.) may be used. In this regard, the mold 51 and the pin 72 may be selected accordingly. For example, a nineteen GA needle 10 may require a mold 51 with a larger cavity and/or a thicker pin 72 as compared to a twenty-two GA needle 10. Within this in mind, the septum/pin mount 70 and/or the plate 50 can be interchangeable with other septum/pin mounts 70 and/or the plates 50, each exhibiting different sized pins 72 and molds 51, respectively. This can be achieved by unfastening the pin-mount fasteners 53 and removing the plate 50 and/or septum/pin mount 70 to replace it or them with another.

Figure 8A:
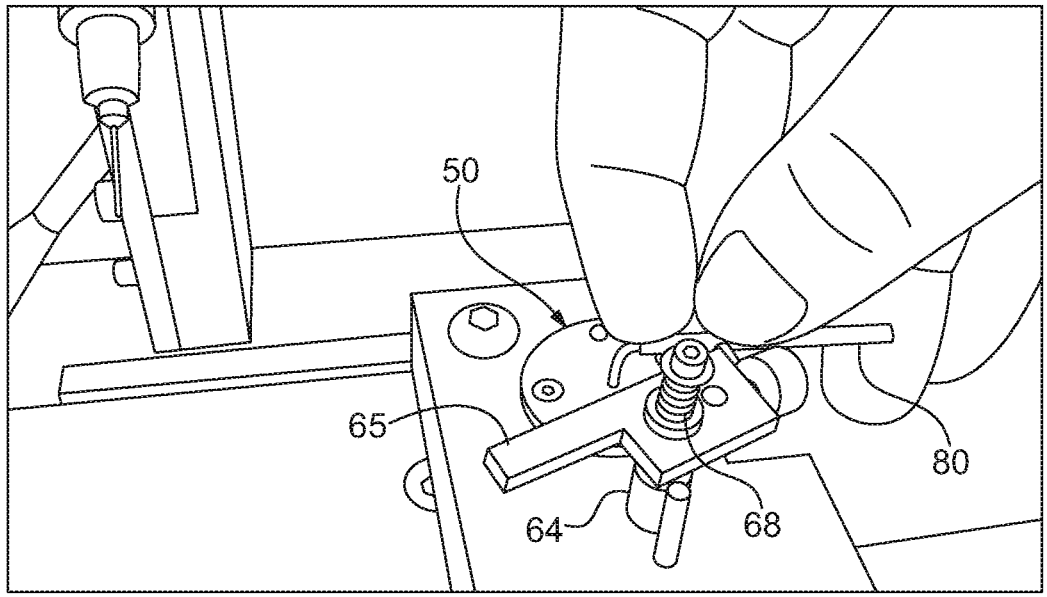
FIGS. 8A-8B show a needle being inserted into a mold of a plate, and the needle inserted into a mold with a spring-loaded swivel arm immobilizing the needle, respectively.
Figure 8B:
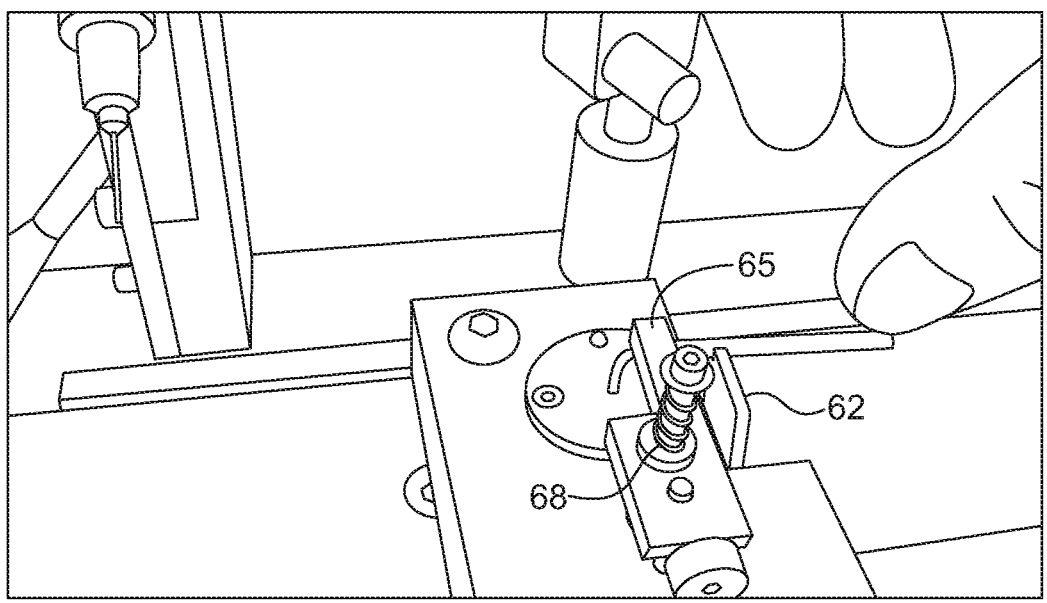
Figure 9A:
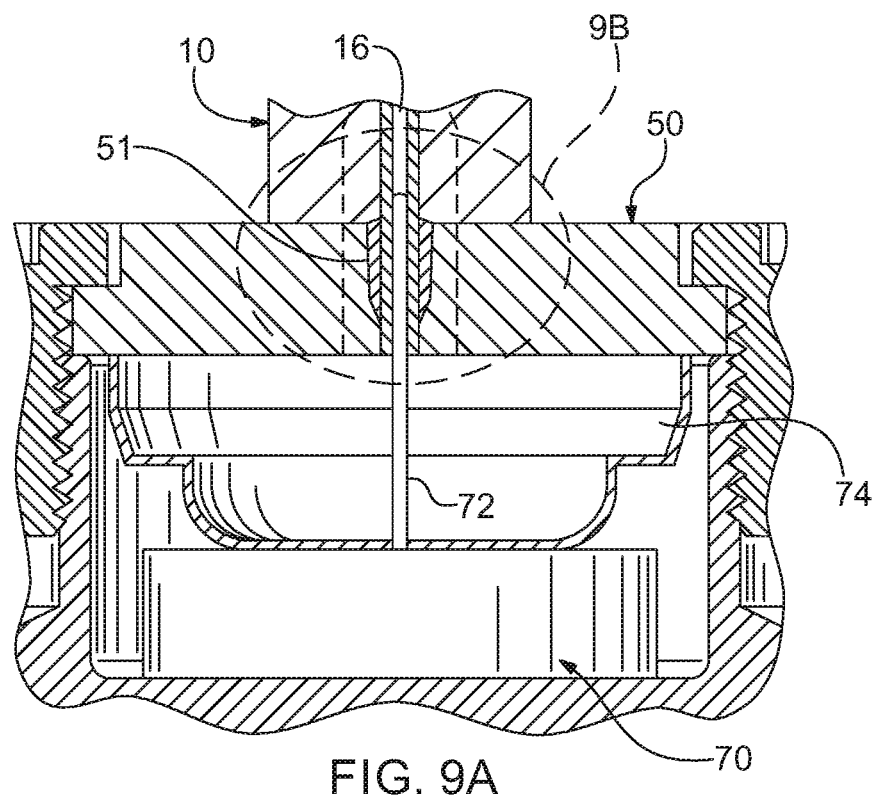
FIGS. 9A-9B show a cross-sectional view of a septum/pin mount pocket with the needle connector end inserted into the mold, and a cross-sectional view of the mold with the needle connector end positioned within the mold, respectively.
Figure 9B:
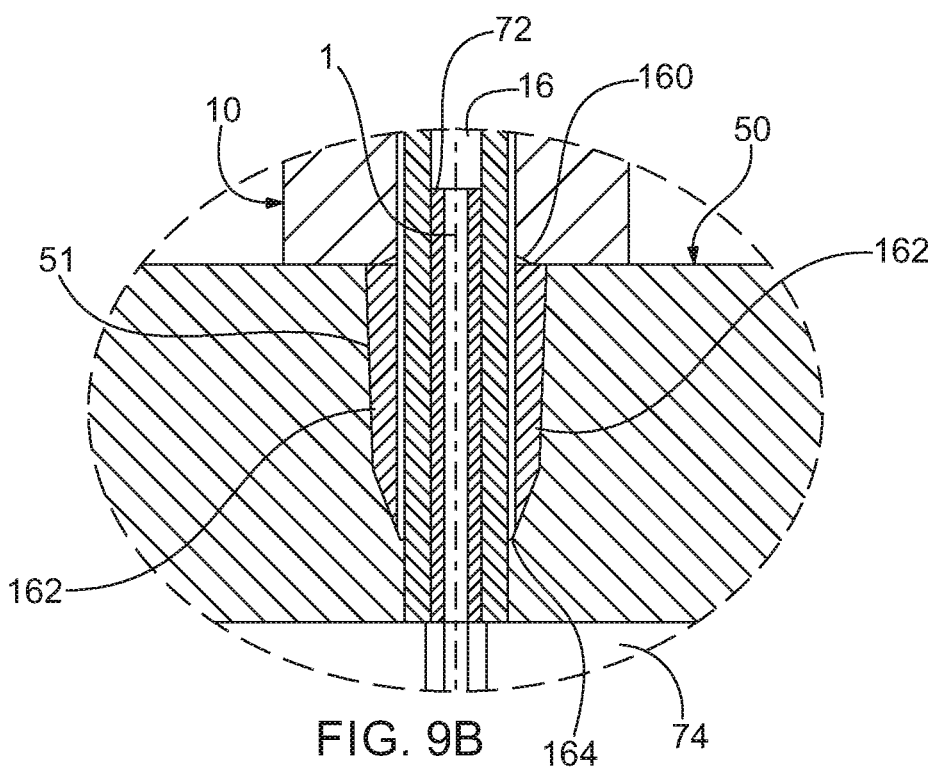

FIGS. 8A-8B show a needle 10 being inserted into the mold 51 of the plate, and the needle inserted into the mold 51 with the spring-loaded swivel arm 65 immobilizing the needle 10, respectively. FIGS. 9A-9B show a cross-sectional view of the septum/pin mount pocket 66 with the needle connector end 12 inserted into the mold 51, and a cross-sectional view of the mold 51 with the needle connector end 12 positioned within the mold 51, respectively. With reference to FIGS. 8A-8B and 9A-9B, at least the needle tip 14 can be covered with a protective sleeve 80 or sheath so as to reduce the occurrence of puncture or other injury that may otherwise occur due to exposure of the needle tip 14 to personnel handling the needle 10. The protective sleeve 80 can be a polymer, silicon, or rubber tube slid over the needle tip 14. The spring-loaded swivel arm 65 can be rotated about the post 64 so as to be outside a volume of space above the plate 50. The needle connector end 12 can then be inserted through the mold 51 by allowing the pin 72 to insert into the needle aperture 16 of the needle 10. Further, where the needle shaft 18 exhibits an angled structure (e.g., a ninety-degree angle), a portion of the needle shaft 18 can be made to rest upon the needle bracket 62. The spring-loaded swivel arm 65 can then be elevated with respect to the post 64 by compressing the spring 68, thereby creating clearance for the spring-loaded swivel arm 65 to rotate inside the volume of space above the plate 50 and over top of the needle shaft 18.

Once the spring-loaded swivel arm 65 is rotated over the needle shaft 18, the spring 68 can be allowed to expand to cause the arm 65 to make contact with the needle shaft 18 and/or protective sleeve 80 and immobilize the needle 10 between the arm 65 and the needle bracket 62. This may be done to ensure that the needle connector end 12 is properly placed and aligned within the mold 51 and to ensure that the needle 10 does not move while forming the formation 20. For example, a proper placement and alignment can include the pin 72 being inserted into the needle aperture 16 of the needle connector end 12 with the longitudinal axis 1 being coaxial with the pin 72. Proper placement and alignment can further include the distal end 13 of the needle connector end 12 being adjacent the septum 74, which may include abutting against the septum 74. Further, proper placement and alignment can include the distal end 13 of the needle connector end 12 being flush with an upper surface of the septum 74. In some embodiments, the needle bracket 62 can be adjustable in height to further aid in facilitating proper placement and alignment. (See FIG. 6B). For example, the needle bracket 26 can be raised or lowered and locked in place at a desired height to ensure that when a portion of the needle shaft 18 rests upon the needle bracket 62, the pin 72 and the needle aperture 16 of the needle connector end 12 are coaxial. This can include the pin 72 and the longitudinal axis 1 being coaxial. Being properly placed and aligned can be referred to as seating the needle connector end 12 within the mold 51. As can be seen in FIG. 9B, seating the needle connector end 12 within the mold 51 can result in the mold 51 being situated around the needle outer surface 11.

As noted above, the mold 51 may be used to generate at least one formation 20 on a needle connector end 12 of a needle 10. The mold 51 can be formed into a plate 50 as at least one cavity having an open top 160 and sidewalls 162 conjoined with a bottom 164. The bottom 164 may be formed into a portion of the plate 50. The at least one cavity may be configured for receiving the needle connector end 12, and the mold can be further configured for receiving first curable material 40 introduced within the at least one cavity adjacent the needle connector end 12 outer surface 11. At least one of the a portion of the sidewalls 162 and the bottom 164 may substantially conform to a portion of the needle connector end 12 so that a contact between the needle connector end 12 and the sidewalls 162 and/or bottom 164 forms a fluid seal to prevent the first curable material 40, in its liquid form, from traveling into the needle aperture 16 or needle lumen. As can be seen in FIG. 9B, upon the first curable material 40 transitioning to the solid form, the at least one formation 20 may take a shape that substantially matches a profile of the at least one cavity. In some embodiments, thee profile of the at least one cavity can generate a fill space to receive the first curable material 40. The fill space may be adjacent the needle connector end 12 outer surface 11. In some embodiments, the fill space may surround an entire circumference of at least a portion of the needle connector end 12 outer surface 11. Further, the portion of the sidewalls 162 that substantially conforms to a portion of the needle connector end 12 can prevent the first curable material 40, in its liquid form, from traveling to a distal end 13 of the needle connector end 12, wherein the distal end 13 of the needle connector end 12 may rest upon the bottom 164. In at least one embodiment, the profile of the at least one cavity exhibits a tapered shape. With some embodiments, the profile of the at least one cavity may exhibit an elongated shape with a conical shaped nose portion leading to a base portion. In at least one embodiment, the at least one cavity can be a single cavity, and the profile of the single cavity may be configured to generate a single formation.

Figure 10:
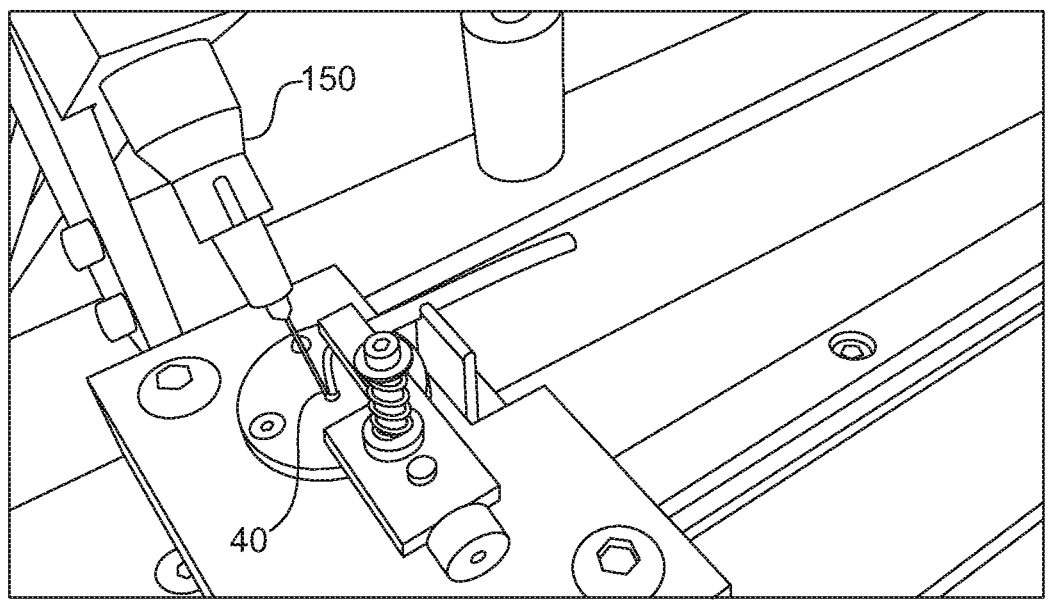
FIG. 10 shows first curable material being inserted into a mold with a needle connector end in the mold.

Referring to FIG. 10, the first curable material 40 can then be introduced into the mold 51 to at least partially fill the mold 51. The first curable material 40 can then be exposed to UV radiation to cause the first curable material 40 to harden into the shape of the mold 51, or at least the shape of a partial portion of the mold 15 into which the first curable material 40 is residing. Further, curing the first curable material 40 can cause the first curable material 40 to adhere to at least a portion of the outer surface 11 of the needle 10 that is within the mold 51.

Figure 11:
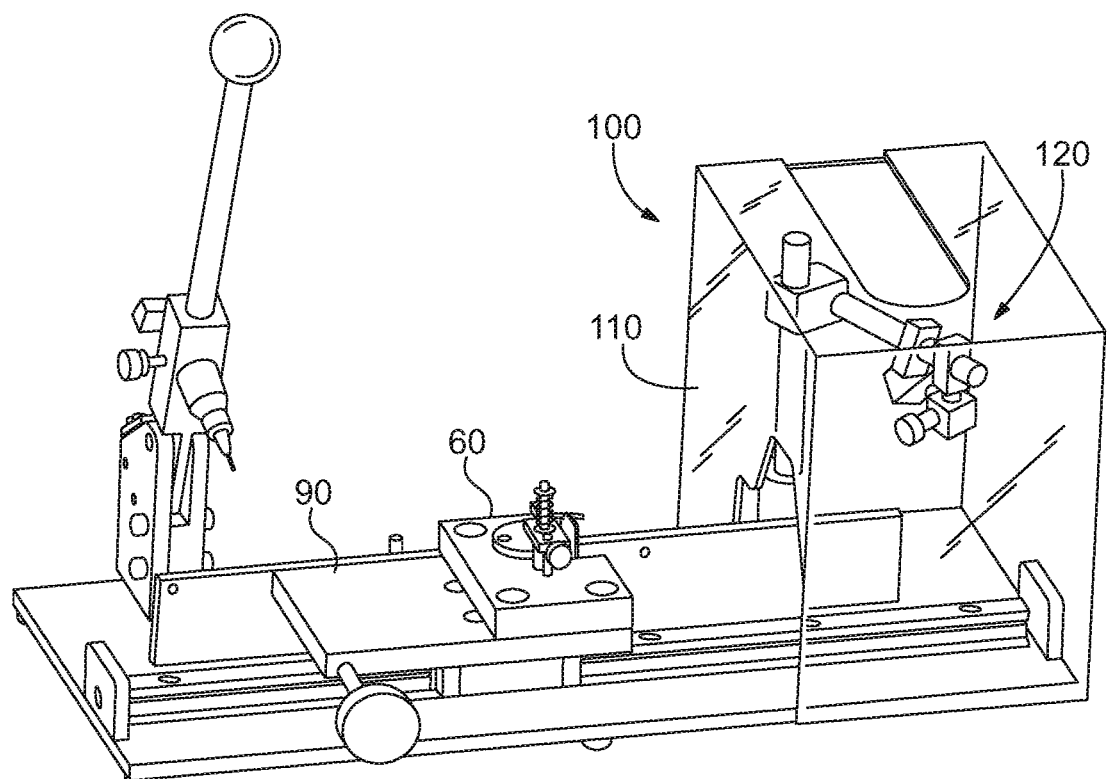
FIG. 11 shows an actuating slide track and an ultraviolet emitter assembly that may be used with the method.

Referring to FIG. 11, causing the first curable material 40 to harden can be achieved by placing the support 60 on an actuating slide track 90 that can slide the support 60 to and from a UV emitter assembly 100. The UV emitter assembly 100 can include a UV protective hood 110 (i.e., UV filtering and/or absorbing) structure than prevents UV radiation from exiting a region of space within the hood 110. The UV emitter assembly 100 can further include at least one first UV emitter 120 to emit electromagnetic radiation at a frequency within the UV spectrum. The support 60, along with the needle 10 and first curable material 40, can be slid within the UV emitter hood 110, where the first curable material 40 can be exposed to UV radiation to cause the first curable material 40 to cure, thereby forming the formation 20. After curing, the support 60, along with the needle 10 and formed formation 20, can be slid from the UV emitter hood 110.

Figure 12:
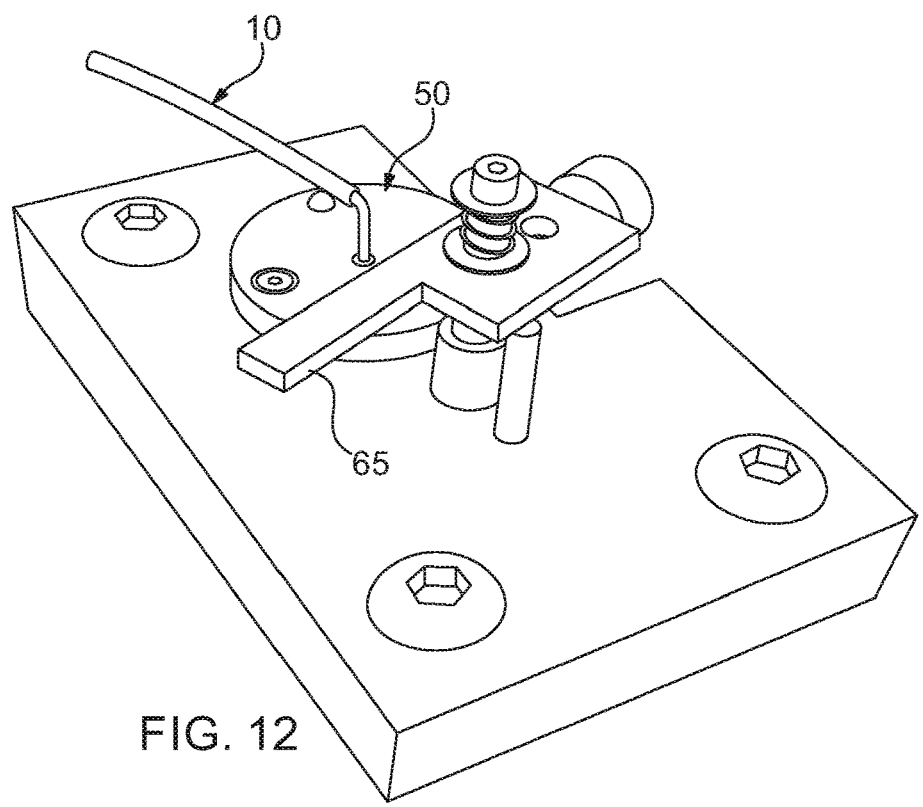
FIG. 12 shows a needle within a mold after the first curable material has been cured.
Figure 13:
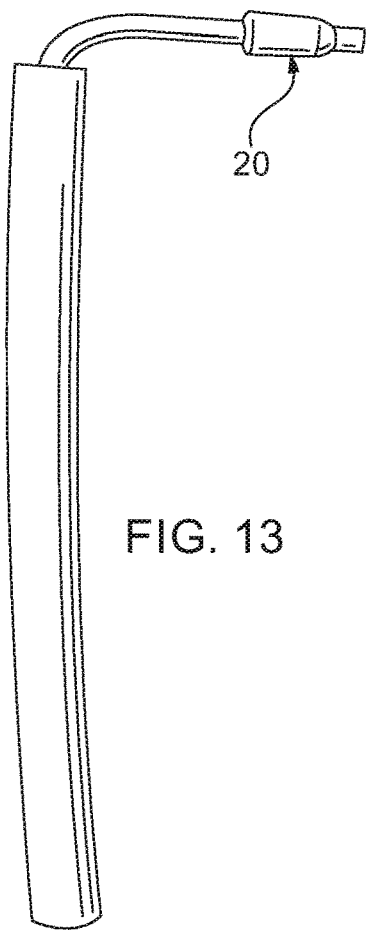
FIG. 13 shows a needle connecter end with a formation after the needle has been removed from the mold.

Referring to FIG. 12, the spring-loaded swivel arm 65 can then be raised in elevation for clearance above the needle shaft 18 and rotated so as to be outside the volume of space above the plate 50. Referring to FIG. 13, the needle 10 can then be removed from the mold 51. The tapered shape of the base 22 of the formation 20, as well as the Teflon® material of the plate 50, can aid in easing the removal of the needle connector end 12 from the plate 50. As shown in FIG. 13, the hardened first curable material 40 takes the shape of the mold 51 to form the formation 20.

Figure 14A:
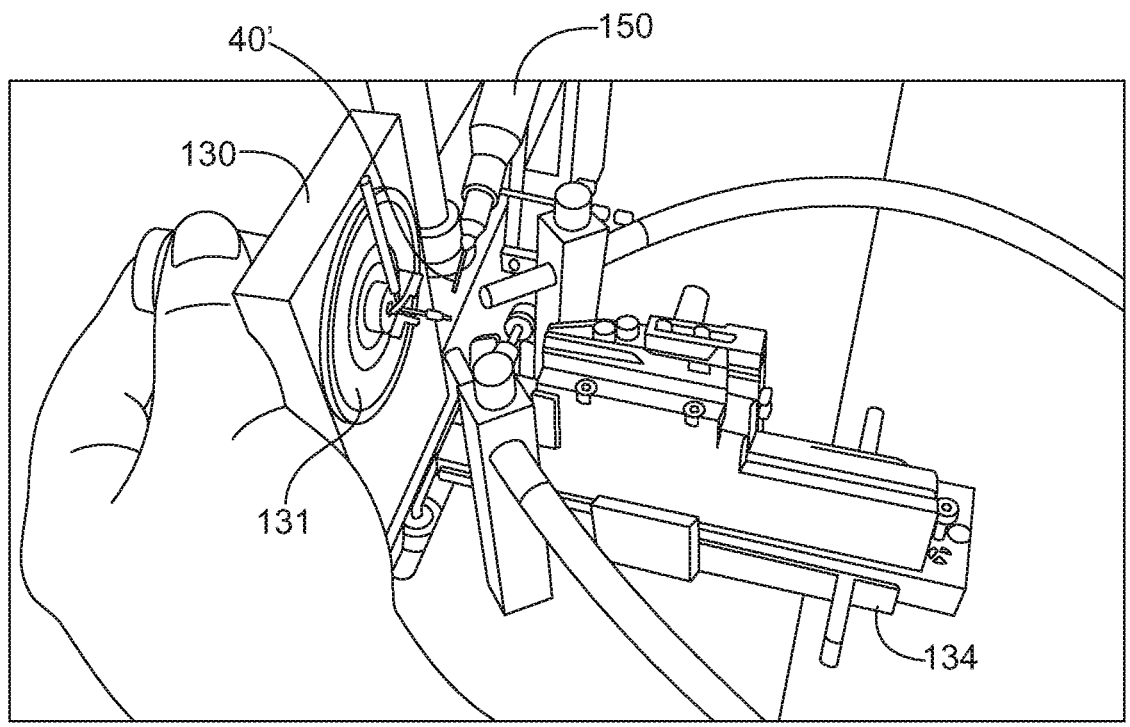
FIG. 14A shows the needle held in place for an application of second curable material.
Figure 14B:
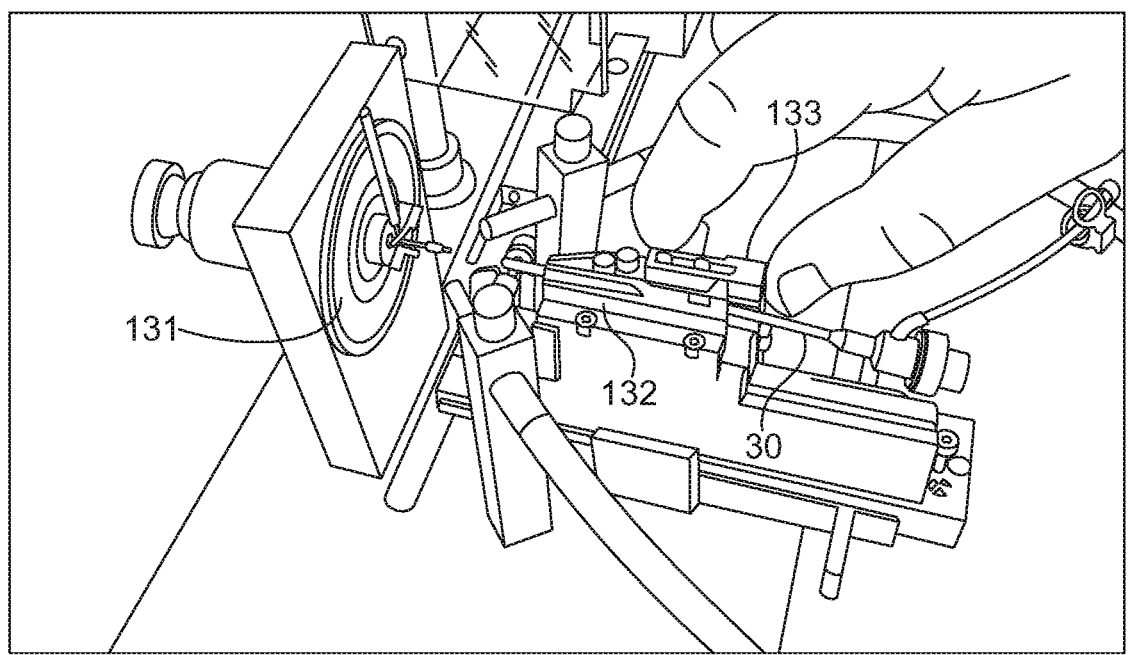
FIG. 14B shows the engagement between the needle and the adapter, wherein the needle connector end is inserted into a lumen of the adapter.
Figure 14C:
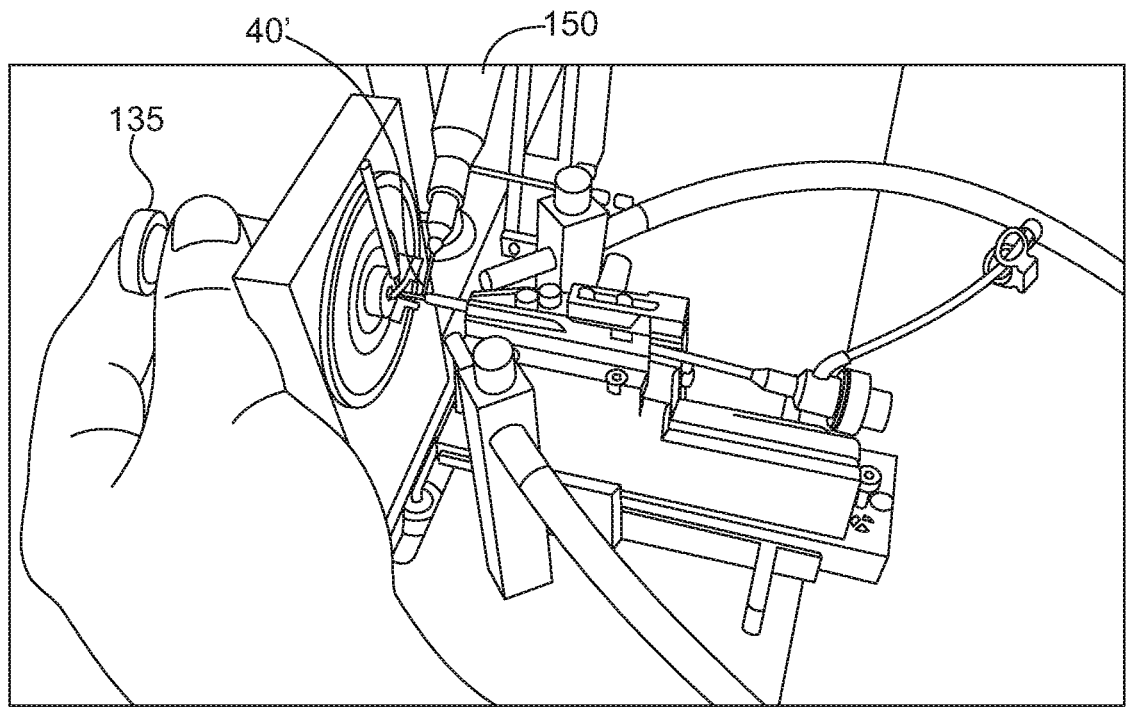
FIG. 14C shows the application of additional second curable material disposed onto a first distal end of the adapter and/or needle connector end.

FIG. 14A shows the needle 10 clamped within a second clamp 130 to be held in place for an application of the second curable material 40'. FIG. 14B shows the engagement between the needle 10 and the adapter 30, wherein the needle connector end 12 is inserted into the lumen 32 of the adapter 30. FIG. 14C shows the application of additional second curable material 40' disposed onto the first distal 33 end of the adapter 30 and/or needle connector end 12. Referring to FIGS. 14A-14C, the needle 10 can be placed into a second clamp 130, which may include a rotatable spring-clamp assembly. The needle shaft 18 can be secured within the second clamp 130 so that the needle connector end 12 extends perpendicularly from a rotator 131 of the rotatable spring-clamp assembly 130. Once secured, the second curable material 40' can be applied to at least a portion of the needle connector end 12, which can be performed with the gun applicator 150. As the second curable material 40' is being applied to the portion of the needle connector end 12, the rotator 131 can be rotated to facilitate an even distribution of the second curable material 40' around a circumference of the needle connector end 12, wherein rotating the rotator 131 can cause the needle connector end 12 to rotate along with the rotator 131.

As seen in FIG. 14B, the rotatable spring-clamp assembly 130 can further include an adapter guide 132 to temporarily secure the adapter 30 and align the lumen 32 of the adapter 30 with the needle connector end 12. Grippers 133, which may be spring-actuated, can be included with the guide to secure the adapter 30 with the adapter guide 132. The adapter can further include a slide block 134 that can facilitate translation of the adapter guide 132 to and from the rotator 131. When the needle 10 is within the rotatable spring-clamp assembly 130 and the adapter 30 is within the adapter guide 132, translation of the slide block 134 toward the rotator 131 can cause the lumen 32 to receive the needle connector end 12 with the formation 20 formed thereon. Further, as the slide block 134 is advanced toward the rotator 131, the rotator 131 can be rotated (causing the needle connector end 12 to rotate along with it) to facilitate easier insertion of the needle connector end 12 within the lumen 32 of the adapter 30.

The adapter 30 can be slid over the needle connector end 12 until a distal end 31 of the adapter 30 convers at least a portion of the formation 20 (i.e., a portion of the formation 20 is within the lumen 32 of the adapter 30). In some embodiments, the adapter 30 can be slid over the needle connector end 12 until a distal end 31 of the adapter 30 convers at least a portion of the base bottom 23 (i.e., a portion of the base bottom 23 is within the lumen 32 of the adapter 30). In further embodiments, the adapter 30 can be slid over the needle connector end 12 until a distal end 31 of the adapter 30 convers the entire formation 20 and the second curable material 40' (i.e., the entire formation 20 and the second curable material 40' is within the lumen 32 of the adapter 30). Additional second curable material 40' can then be disposed on the first distal end 33 the adapter 30 and/or the needle connector end 12, as shown in FIG. 14C. As the second curable material 40' is being applied, the rotator 131 can be rotated to ensure that the application of the second curable material 40' evenly covers an entire circumference of the first distal end 33 the adapter 30 and/or the needle connector end 12. The rotator 131 can be rotated by grasping a rotator handle 135 and forcing it to rotate, thereby causing the rotator 131 to rotate. The grippers 133 can then be actuated to release the adapter 30 from the adapter guide 132 and allow the slide block 134 to be slid away from the rotator 131, which can include sliding the slide block 134 relative to the adapter 30 that is now engaged with the needle 10.

Figure 15:
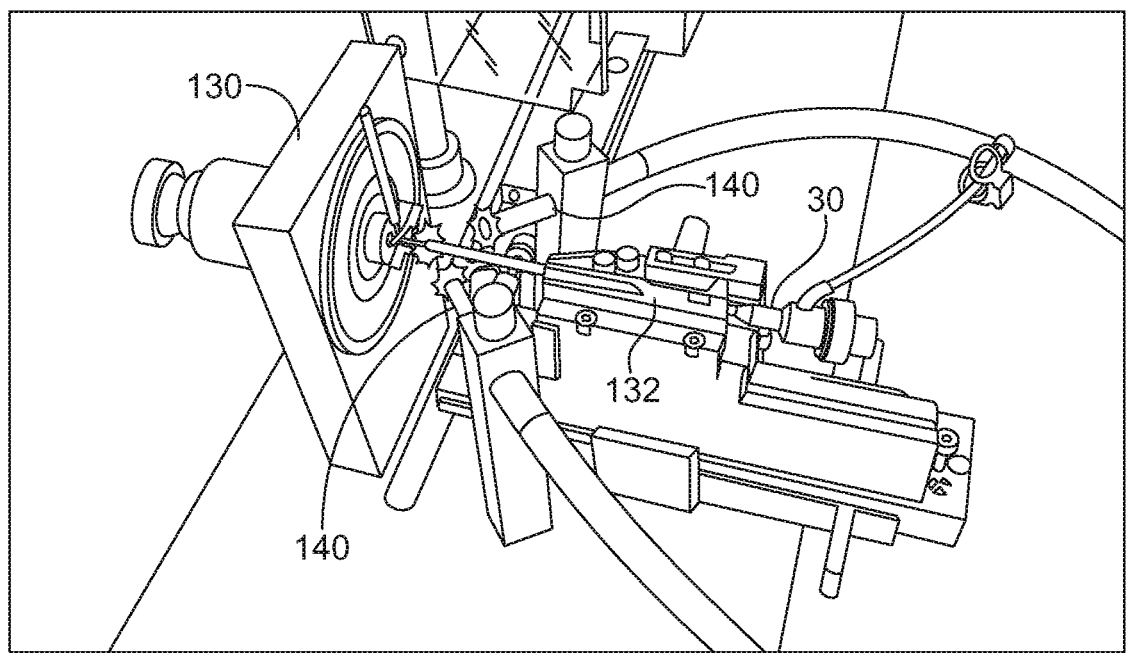
FIG. 15 shows the second curable material being exposed to UV radiation.

FIG. 15 shows the second curable material being exposed to UV radiation. The second curable material 40' can be exposed to UV radiation until the second curable material 40' hardens and/or adheres to at least one of the needle connector end 12, the needle shaft 18, the formation 20, and the adapter 30. In some embodiments, the spring-clamp assembly 130 can include at least one second UV emitter 140 to emit electromagnetic radiation at a frequency within the UV spectrum. The needle 10 can then be removed from the rotatable spring-claim assembly 130, which may include removing the adapter 30 from the adapter guide 132. The resultant structure is a needle 10 with a needle connector end 12 having a formation 20, where the needle connector end 12 is bonded to an adapter 30, as shown in FIG. 5G.

While embodiments disclose use of UV curable materials 40, 40' and UV emitters 120, 140, other curable materials that cure at different frequencies of electromagnetic radiation can be used. Consequently, other electromagnetic emitters can be used to emit radiation at frequencies other than within the UV spectrum to cause the curable materials to cure. Further other materials can be used that transition from a liquid to solid. These can transition based on exposure to air, exposure to a certain temperature, exposure to ultrasonic wave, etc. These can include, but are not limited to monomer glues, polymer glues, polystyrene composites, epoxy, etc.

In further embodiments, the curable materials 40. 40' can be applied in any of the steps above as a liquid and subsequently hardened by curing. Applying a liquid curable material can be achieved through a gun applicator 150 (see FIGS. 5A-5B, 5D-5E, 10, 14A, and 14C).

An assembly including the innovative bond between a needle 10 and an adapter 30 has been tested and contrasted with traditional bonding methods. Traditional bonding methods consist of applying a volume of glue on at a junction between the needle and the adapter, and in particular without use of the formation 20 as described above. For the traditional bonding methods, the test included a plurality of nineteen GA, twenty GA, and twenty-two GA needles 10, each bonded in a traditional manner to an adapter 30. A first group (V-9762) was subjected to a Medrad Power Injection Simulation Test ("Medrad Test") and a second group (V-9763) was subjected to a HBLT Static Burst Power Injection Simulation Test ("HBLT Test"). For the innovative bonding method, the test included a plurality of nineteen GA and twenty-two GA needles 10, each bonded in the innovative manner to an adapter 30. The plurality of needle and adapter assemblies (V-9859) were subjected to a Medrad Test and a HBLT Test.

Both the Medrad Test and the HBLT Test included subjecting the needle and adapter assemblies to an initial (or pre-injection) air leak test and initial (or pre-injection) liquid leak test. The liquid leak tests were conducted by injecting a liquid through the needle and adapter assemblies at a pressure within a range from 45 pounds per square inch ("psi") to 50 psi. After passing an air and liquid leak test (i.e., exhibiting no leaks), each needle and adapter assembly was injected with contrast agent under a differential pressure. Subjecting the needle and adapter assemblies was done for a certain time duration at a certain flow rate to generate a cycle. The cycle was repeated for each needle and adapter assembly to determine at which cycle the needle and adapter assembly would leak. The needle and adapter assemblies that did not experience a leak were then subjected to post-injection air leak test and a post-injection liquid leak test (e.g., similar to the initial air and liquid leak tests). In regards to the Medrad Power Injection Simulation, a leak was visually observed by a technician during the power injection cycle. In regards to the HBLT Static Burst Power Injection Simulation, the leak rate alarm was detected by the HBLT static burst tester machine. A leak can be triggered in two different ways. The first being a loss of pressure >30 psi during the ramp up stage (the "ramp up stage" is when the HBLT begins pressurizing the assembly until it reaches the target static burst pressure, which in this case was 357 psi). The second is a loss of pressure >5 psi/second or a total of 57 psi during the dwell time stage (the "dwell" is the duration of time the assembly is stabilized and held at the target pressure).

For the Medrad Tests, the needle and adapter assemblies were subjected to the following conditions:

TABLE II

Medrad Test Parameters for 19 GA Needles with Traditional Bonding Method (V9762)
1.5" 19Ga. In-House Safety Huber Needle

|  | Flow Rate (ml/s) | Machine Pressure (psi) |
| --- | --- | --- |
| Average | 4.80 | 322.18 |
| Std Dev. | 0.02 | 0.80 |
| Max | 4.80 | 324.00 |
| Min | 4.70 | 321.00 |

TABLE III

Medrad Test Parameters for 20 GA Needles with Traditional Bonding Method (V9762)
1.5" 20Ga. In-House Safety Huber Needle

|  | Flow Rate (ml/s) | Machine Pressure (psi) |
| --- | --- | --- |
| Average | 3.91 | 327.24 |
| Std Dev. | 0.07 | 1.05 |
| Max | 4.10 | 329.00 |
| Min | 3.80 | 325.00 |

TABLE IV

Medrad Test Parameters for 22 GA Needles with Traditional Bonding Method (V9762)
1.5" 22Ga. In-House Safety Huber Needle

|  | Flow Rate (ml/s) | Machine Pressure (psi) |
| --- | --- | --- |
| Average | 1.59 | 329.88 |
| Std Dev. | 0.03 | 0.78 |
| Max | 1.60 | 332.00 |
| Min | 1.50 | 329.00 |

TABLE V

Medrad Test Parameters for 19 GA Needles with Innovative Bonding Method (V-9859)

| Part Description | 19 GA × 1½" Needle |
| --- | --- |
| Precondition Temp. | 37 +/− 2° C. |
| Contrast Media | Visipaque 320 ™ 12951401 |
| Rise/Fall(s) 0.5 | Injection Duration (s) 30.3 sec |
| Flow Rate (m/s) 5 cc/sec | Pressure Limit (psi) 325 psi |
| Volume (ml) 150 cc | Delay(s) 0 |
| Collection Bath Temp. 37° +/− 1° C. | Test Bath Temp. 37° +/− 1° C. |

TABLE VI

Medrad Test Parameters for 22 GA Needles with Innovative Bonding Method (V-9859)

| Part Description | 22 GA Huber Needle prototype |
| --- | --- |
| Precondition Temp. | NA |
| Contrast Media | Visipaque 320 ™ 12951401 |
| Rise/Fall(s) 0.5 | Injection Duration (s) 75.3 sec |
| Flow Rate (m/s) 2 cc/sec | Pressure Limit (psi) 325 psi |
| Volume (ml) 150 cc | Delay(s) 0 |
| Collection Bath Temp. 37° +/− 1° C. | Test Bath Temp. 37° +/− 1° C. |

For the HBLT Tests, the needle and adapter assemblies were subjected to the following conditions:

TABLE VII

HBLT Test Parameters for 19 GA Needles with Traditional Bonding Method (V-9763)
19GA × 1.5" Y-Set
HBLT Program - HN1920 10X

| Sample | Max Pressure (psi) | Event Pressure (psi) | Event Location |
| --- | --- | --- | --- |
| 1 | N/A | N/A | Sample excluded (V-9762 failure) |
| 2 | N/A | N/A | Sample excluded (V-9762 failure) |
| 3 | 361 | No event | no event |
| 4 | 361 | No event | no event |
| 5 | 360 | 357 | Leak Rate Alarm, 1st cycle |
| 6 | 361 | No event | no event |
| 7 | 360 | No event | no event |
| 8 | 361 | No event | no event |
| 9 | 361 | 361 | Leak Rate Alarm, 1st cycle |
| 10 | 361 | No event | no event |
| AVG | 360.75 | 359 | |
| SD | 0.46 | 2.83 | |
| Max | 361 | 361 | |
| Min | 360 | 357 | |

TABLE VIII

HBLT Test Parameters for 20 GA Needles with Traditional Bonding Method (V-9763)
20GA × 1.5" Y-Set
HBLT Program - HN1920 10X

| Sample | Max Pressure (PSI) | Event Pressure | Event Location |
| --- | --- | --- | --- |
| 1 | 361 | no event | no event |
| 2 | 360 | no event | no event |
| 3 | 361 | no event | no event |
| 4 | 360 | no event | no event |
| 5 | 360 | no event | no event |
| 6 | 361 | 357 | Leak Rate Alarm, 6th cycle |
| 7 | 360 | no event | no event |
| 8 | 360 | 350 | Up Burst Alarm, 1st cycle |
| 9 | 361 | no event | no event |
| 10 | 361 | no event | no event |
| AVG | 328.1 | 353.5 | |
| SD | 102.63 | | |
| Max | 361 | | |
| Min | 36 | | |

TABLE IX

HBLT Test Parameters for 20 GA Needles with Traditional Bonding Method (V-9763)
22GA × 1.5" Y-Set
HBLT Program - HN22 10X

| Sample | Max Pressure (PSI) | Event Pressure | Event Location |
| --- | --- | --- | --- |
| 1 | 361 | no event | no event |
| 2 | 361 | no event | no event |
| 3 | 360 | no event | no event |
| 4 | 365 | no event | no event |

TABLE IX-continued

HBLT Test Parameters for 20 GA Needles with Traditional Bonding Method (V-9763)
22GA × 1.5" Y-Set
HBLT Program - HN22 10X

| Sample | Max Pressure (PSI) | Event Pressure | Event Location |
|---|---|---|---|
| 5 | 360 | no event | no event |
| 6 | 360 | no event | no event |
| 7 | 360 | no event | no event |
| 8 | 360 | no event | no event |
| 9 | 360 | 356 | leak during dwell time, 2nd cycle |
| 10 | 364 | no event | no event |
| AVG | 361.1 | N/A | |
| SD | 1.85 | | |
| Max | 365 | | |
| Min | 360 | | |

TABLE X

HBLT Test Parameters for 22 GA Needles with Innovative Bonding Method (V-9859)

| Part Description | 22 GA Huber Needle Prototype |
|---|---|
| Sterilization Load | NA |
| Precondition Temp. | Ambient |
| Tested pressure (psi) | 360 psi |

For the Medrad Test with the V-9762 group (traditional bonding method), the test simulated power injection of contrast agent through the In-House Safety Huber Needle Samples and 5F Ti Dignity Low Profile Port. In-House Safety Huber Needles were exposed to 1× EtO sterilization. All samples passed pre-and post-injection air and liquid leak testing (there were two nineteen GA samples that leaked during power injection and were not subjected to the post-injection air and liquid leak). All 20Ga and 22Ga samples withstood 5 cycles of power injection simulation at 5 cc/sec and 2 cc/sec respectively without exhibiting any physical damage. Two nineteen GA samples leaked at the needle/collar area, where one sample leaked on the $2^{nd}$ cycle and another sample leaked on the $5^{th}$ cycle.

For the HBLT Test with the V-9763 group (traditional bonding method), the testing was performed to simulate power injection on the In-House Safety Huber Needles. Test samples were tested on a HBLT-01 Hydraulic Burst/Leak Tester at 357 psi for 10 cycles using programs "HN1920 10×" and "HN22 10×". Five total samples were found to leak/burst during testing, where the leak occurred at the collar-needle joint during static burst power injection simulation testing on the HBLT. Two nineteen GA samples leaked on the $1^{st}$ cycle. Another nineteen GA sample triggered a leak rate alarm 11.0 seconds into the dwell time. Another nineteen GA sample burst on the up ramp at 360 psi. A twenty GA sample leaked on the $1^{st}$ cycle and another twenty GA sample leaked on the $6^{th}$ cycle. Another twenty GA sampled triggered a leak rate alarm 10.6 seconds into the dwell time. Another twenty GA sample burst 22.4 seconds into the dwell time at 350 psi. A twenty-two GA sample leaked on the $2^{nd}$ cycle as it triggered a leak rate alarm 15.7 seconds into the dwell time.

For the Medrad Test with the V-9859 group (innovative bonding method), no leaks were detected for any sample up to 5 cycles. For the HBLT Test with the V-9859 group (innovative bonding method), all the samples survived at least 28 cycles, and some lasted as long as 44 cycles. The table below shows the results of the various tests, indicating the beneficial results of the innovative bonding method contrasted with the inferior results of the traditional bonding method.

TABLE XI

Results of the Medrad and HBLT Tests
Needle-To-Tubing Bonding Method Comparison

| | Old Bonding Method | | | | | |
|---|---|---|---|---|---|---|
| | Test Number | | | | | |
| | V-9762 | | | V-9763 | | |
| | Type of Test | | | | | |
| | Medrad Power Injection Simulation | | | HBLT Static Burst Power Injection Simulation | | |
| | Bonding Method | | | | | |
| | Traditional Gluing Method | | | Traditional Gluing Method | | |
| | Number of Cycles | | | | | |
| | 5 Cycles | | | 10 Cycles | | |
| | Needle Gauge Size | | | | | |
| | 19 Ga | 20 Ga | 22 Ga | 19 Ga | 20 Ga | 22 Ga |
| Testing Sample Size | 10 | 10 | 10 | 8 | 10 | 10 |
| Number of Failures | 2 | 0 | 0 | 2 | 2 | 1 |
| Cycle Number that Sample Leaked at | 2nd, 5th | N/A | N/A | 1st, 1st | 6th, 1st | 2nd |
| Average Cycle Completed | 4.6 | 5 | 5 | 7.75 | 8.7 | 9.1 |

TABLE XI-continued

Results of the Medrad and HBLT Tests
Needle-To-Tubing Bonding Method Comparison

| | NewBonding Method | | | |
|---|---|---|---|---|
| | Test Number | | | |
| | V-9859 | | V-9859 | |
| | Type of Test | | | |
| | Medrad Power Injection Simulation | | HBLT Static Burst Power Injection Simulation | |
| | Bonding Method | | | |
| | New Glue Barb Method | | New Glue Barb Method | |
| | Number of Testing Cycles | | | |
| | 5 Cycles | | 50 Cycles | |
| | Needle Gauge Size | | | |
| | 19Ga | 22Ga | 19Ga | 22Ga |
| Testing Sample Size | 10 | 10 | 10 | 10 |
| Number of Failures | 0 | 0 | 9* | 1 |
| Cycle Number that Sample Leaked at | N/A | N/A | 28th, 47th, 44th, 44th, 43rd, 43rd, 25th, 23rd, 32nd | 48th |
| Average Cycle Completed | 5 | 5 | 37.9 | 49.8 |

*High failure rate was due to the aggressive nature of the test after increasing # of cycles from 10 to 50.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An assembly, comprising:
   a needle comprising a needle connector end, a needle tip, a needle shaft extending between the needle connector end and the needle tip, and an aperture extending through the needle from the needle tip to the needle connector end;
   at least one formation formed from a first curable material deposited and cured on at least a portion of the needle connector end; and,
   an adapter having a lumen,
      wherein the needle connector end and the at least one formation are accommodated within the adapter lumen;
      wherein the adapter is bonded to at least one of the needle connector end and the at least one formation by a second curable material disposed on at least a portion of at least one of the needle connector end and the at least one formation;
      wherein the bond prevents movement of the needle relative to the adapter in at least a forward longitudinal direction; and
      wherein the at least one formation prevents disengagement of the adapter from the needle connector end when fluid is introduced through the adapter lumen into the needle aperture.

2. The assembly of claim 1, wherein the formation prevents disengagement of the adapter from the needle connector end when fluid is introduced through the adapter lumen into the needle aperture at a pressure of at least 400 psi.

3. The assembly of claim 1, wherein the formation prevents disengagement of the adapter from the needle connector end when fluid is introduced through the adapter lumen into the needle aperture at a pressure ranging from 400 psi to 600 psi.

4. The assembly of claim 1, wherein the first curable material and the second curable material are the same.

5. The assembly of claim 1, wherein the first curable material and the second curable material are different.

6. The assembly of claim 1, wherein the adapter is at least one of a catheter, a cannula, a tubing, and a connector of a Huber needle assembly.

7. The assembly of claim 1, wherein the at least one formation has an elongated shape with a conical shaped nose portion leading to a base portion.

8. The assembly of claim 7, wherein the at least one formation is a single formation disposed around an entire circumference of an outer surface of a portion of the needle connector end.

9. The assembly of claim 7, wherein the second curable material is disposed at a bottom of the base portion.

10. The assembly of claim 1, wherein each of the first curable material and the second curable material is a thermosetting polymer, or resin that hardens and/or adheres upon exposure to electromagnetic radiation.

11. The assembly of claim 10, wherein the electromagnetic radiation is UV radiation.

12. The assembly of claim 10, wherein the first curable material and the second curable material are each selected from the group consisting of polyester, polyurethane, epoxy resin, polyimides, and acrylic adhesives.

13. The assembly of claim 12, wherein the first curable material and the second curable material are each an acrylic adhesive.

* * * * *